United States Patent
Merchant

(10) Patent No.: US 10,155,076 B2
(45) Date of Patent: Dec. 18, 2018

(54) METHOD FOR TREATING DIALYSATE, DIALYSIS SYSTEM, AND METHOD FOR PRE-EVALUATING DIALYSIS PATIENTS FOR TREATMENT WITH SAME

(71) Applicant: Fresenius Medical Care Holdings, Inc., Waltham, MA (US)

(72) Inventor: Stephen Merchant, Oklahoma City, OK (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 625 days.

(21) Appl. No.: 14/723,493

(22) Filed: May 28, 2015

(65) Prior Publication Data
US 2015/0343126 A1 Dec. 3, 2015

Related U.S. Application Data

(60) Provisional application No. 62/004,642, filed on May 29, 2014.

(51) Int. Cl.
*A61M 1/14* (2006.01)
*G16H 10/60* (2018.01)
(Continued)

(52) U.S. Cl.
CPC ............ *A61M 1/14* (2013.01); *A61M 1/1666* (2014.02); *A61M 1/1696* (2013.01); *G06F 19/00* (2013.01);
(Continued)

(58) Field of Classification Search
CPC .... A61M 1/14; A61M 1/1666; A61M 1/1696; A61M 2209/06; A61M 2205/3334; G06F 19/322
See application file for complete search history.

(56) References Cited

U.S. PATENT DOCUMENTS 4,441,538 A * 4/1984 Larkin .................. A61J 1/10
215/247
5,409,477 A * 4/1995 Caron ................... A61M 5/141
128/912
(Continued)

FOREIGN PATENT DOCUMENTS

CN 102510760 A 6/2012
CN 10339419 A 11/2013
(Continued)

OTHER PUBLICATIONS

Communication Relating to the Results of the Partial International Search issued in corresponding International Patent Application No. PCT/US2015/032778 dated Aug. 26, 2015 (7 pages).
(Continued)

*Primary Examiner* — Krishnan S Menon
*Assistant Examiner* — Waqaas Ali
(74) *Attorney, Agent, or Firm* — Kilyk & Bowersox, P.L.L.C.

(57) ABSTRACT

A method for treating dialysate solutions used in dialysis wherein dialysate is treated in an early part of a dialysis treatment session by external infusion of bicarbonate solution into the dialysate circuit to eliminate the need for bicarbonate requirements in concentrates used for preparation of precursor dialysate (priming) solutions and/or for a solid bicarbonate layer in a sorbent cartridge. Dialysate is treated in a latter part of a dialysis treatment session by introduction of sterile dilution water to reduce sodium concentration in the dialysate. The method provides a more efficient and reduced use of dialysate fluids, electrolytes, sorbent cartridge materials, equipment scale, or any combinations of these, while maintaining purity standards and applicable physiological ranges for bicarbonate, sodium, (Continued)

and other dialysate solution components over the course of a dialysis treatment session.

11 Claims, 12 Drawing Sheets

(51) Int. Cl.
*G06F 19/00* (2018.01)
*A61M 1/16* (2006.01)

(52) U.S. Cl.
CPC ..... *G16H 10/60* (2018.01); *A61M 2205/3334* (2013.01); *A61M 2209/06* (2013.01)

(56) References Cited

U.S. PATENT DOCUMENTS

| | | | |
|---|---|---|---|
| 6,136,201 | A | 10/2000 | Shah et al. |
| 6,627,164 | B1 | 9/2003 | Wong |
| 7,566,432 | B2 | 7/2009 | Wong |
| 8,182,692 | B2 | 5/2012 | Gotch |
| 8,220,643 | B2 | 7/2012 | Eisen |
| 8,409,444 | B2 | 4/2013 | Wong |
| 8,497,107 | B2 | 7/2013 | Merchant |
| 8,640,887 | B2 | 2/2014 | Wong |
| 8,647,506 | B2 | 2/2014 | Wong |
| 8,672,145 | B2 | 3/2014 | Eisen |
| 8,733,559 | B2 | 5/2014 | Wong |
| 8,758,626 | B2 | 6/2014 | Wong |
| 2006/0140840 | A1 | 6/2006 | Wong |
| 2010/0078381 | A1 | 4/2010 | Merchant |
| 2010/0078387 | A1 | 4/2010 | Wong |
| 2011/0272337 | A1* | 11/2011 | Palmer ................ A61M 1/1696 210/195.2 |
| 2011/0315611 | A1 | 12/2011 | Fulkerson et al. |
| 2012/0273354 | A1 | 11/2012 | Orhan et al. |
| 2013/0168316 | A1 | 7/2013 | Noguchi et al. |
| 2013/0186759 | A1 | 7/2013 | Lin et al. |
| 2013/0190168 | A1 | 7/2013 | Wong et al. |
| 2013/0230896 | A1 | 9/2013 | Merchant |
| 2013/0256227 | A1* | 10/2013 | Kelly .................. A61M 1/1696 210/638 |
| 2013/0274642 | A1 | 10/2013 | Soykan et al. |
| 2014/0175126 | A1 | 6/2014 | Carlsson et al. |
| 2014/0248204 | A1 | 9/2014 | Wong |
| 2015/0108069 | A1 | 4/2015 | Merchant et al. |

FOREIGN PATENT DOCUMENTS

| | | |
|---|---|---|
| EP | 2263715 A1 | 12/2010 |
| EP | 2494998 A1 | 9/2012 |
| WO | 2011140268 A2 | 11/2011 |
| WO | 2012067585 A1 | 5/2012 |
| WO | 2013040082 A2 | 3/2013 |

OTHER PUBLICATIONS

COBE Centrysystem 3 Dialysis Control Unit "Operator's Manual" COBE Laboratories, Inc., 1988 (233 pages).
"Optiflux Dialyzers," Fresenius Medical Care North America, www.fmcna.com, 2009 (2 pages).
Home Dialysis Central "Ultrapure Dialysate: What, How, and Why," http://www.homedialysis.org/life-at-home/articles/ultrapure-dialysate, May 27, 2014 (4 pages).
International Search Report and Written Opinion issued in corresponding International Patent Application No. PCT/US2015/032778 dated Jun. 3, 2016 (24 pages).
Office Action received in corresponding Chinese Patent Application No. 201580028209.1 dated Jul. 27, 2018 (in Chinese with English translation attached) (10 pages).

* cited by examiner

METHOD FOR TREATING DIALYSATE, DIALYSIS SYSTEM, AND METHOD FOR PRE-EVALUATING DIALYSIS PATIENTS FOR TREATMENT WITH SAME

This application claims the benefit under 35 U.S.C. § 119(e) of prior U.S. Provisional Patent Application No. 62/004,642, filed May 29, 2014, which is incorporated in its entirety by reference herein.

FIELD OF THE INVENTION

The present invention relates to a method for treating dialysate, a dialysis system for carrying out the method, and a method for pre-evaluating dialysis patients as part of a treatment using such a method and/or system.

BACKGROUND OF THE INVENTION

Dialysis is a treatment that removes the waste products and excess fluid which accumulate in the blood as a result of kidney failure. Peritoneal dialysis (PD) and hemodialysis are two forms of dialysis. Hemodialysis is a method of blood purification in which blood is continually removed from the body during a treatment session and passed through a dialyzer (artificial kidney) where metabolic waste and excess water are removed and pH and acid/base balances are normalized. The blood is concurrently returned to the patient's body. The dialyzer is a small disposable device consisting of a semi-permeable membrane. The membrane allows the wastes, electrolytes, and water to cross but restricts the passage of large molecular weight proteins and blood cells. Blood is pumped across one side of the membrane as dialysate is pumped in the opposite direction across the other side of the membrane. The dialysate is highly purified water with salts and electrolytes added. The machine is a control unit which acts to pump and control pressures, temperatures, and electrolyte concentrations of the blood and the dialysate. The average length of one hemodialysis treatment is 3-5 hours. Hemodialysis can be performed as single pass dialysis or sorbent-based dialysis.

Single-pass and sorbent dialysis systems both deliver dialysate to the dialyzer in prescribed amounts to cleanse the blood of impurities, correct the patient's body chemistry, and remove excess fluid. Sorbent dialysis differs from traditional single-pass dialysis in that sorbent systems use less water than single-pass machines and do not require special plumbing. Single-pass systems use approximately 120 liters of water during a typical 4-hour treatment. In single-pass dialysis, a water treatment system is required to continuously pump purified water into the system to be blended with the bicarbonate and acid bath to create the final dialysate. This requires special plumbing to connect the single-pass machine to both the water treatment system and to a drain into which the used dialysate and rejected source water are disposed.

By utilizing sorbent technology, a dialysis system can provide dialysate for 3- to 5-hour dialysis treatments using 6-12 liters of potable tap water. The sorbent cartridge purifies the initial dialysate (formed from the tap water) and continuously recirculates and regenerates the dialysate throughout the treatment. Sorbent dialysis does not require a continuous water source, a separate water purification machine or a floor drain because it continuously regenerates a small volume of dialysate and thus incorporates a water treatment system within the machine. In addition, sorbent systems can use a lower amperage electrical source because they recycle the same small volume of dialysate throughout the dialysis procedure. The heavy duty dialysate pumps and heaters used for large volumes of dialysate in single pass dialysis are not needed. Sorbent dialysis provides a high degree of portability compared to single pass dialysis.

Sorbent dialysis uses a sorbent cartridge, which acts both as a water purifier and as a means to regenerate used (spent) dialysate into fresh dialysate. During a sorbent dialysis treatment, urea is decomposed within the sorbent cartridge, uremic wastes are removed, and dialysate pH and electrolyte balances are maintained. A sorbent cartridge including zirconium phosphate (ZrP) and hydrous zirconium oxide (HZO) ion-exchange materials has been historically used for the REDY (REgenerative DialYsis) system. The REDY sorbent cartridge has several layers through which used dialysate passes. The scheme of the REDY cartridge is shown in FIG. 1. The sorbent cartridge is shown with the inlet and the outlet identified as numeral 11 and numeral 13, respectively. FIG. 2 shows various functions of each layer in a REDY cartridge. The principle of the REDY cartridge is based on the hydrolysis of urea to ammonium carbonate by the enzymatic reaction with urease. FIGS. 1-2 show alumina supported urease. The following equation shows a reaction for urea conversion to ammonia in the presence of urease:

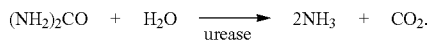

The ammonia and ammonium ions are then removed by the zirconium phosphate in exchange for the hydrogen ions and Na$^+$ ions, which are counter-ions in the cation exchanger. Zirconium phosphate also serves as cation exchanger to remove Ca$^+$, Mg$^+$, K$^+$, and other cations in dialysate. The carbonate from the urea hydrolysis then combines with the hydrogen ions in zirconium phosphate to form bicarbonate, which is delivered to the uremic patient as a base to correct for acidosis. Zirconium phosphate can be represented as inorganic cation exchange material with the molecular structure as shown below:

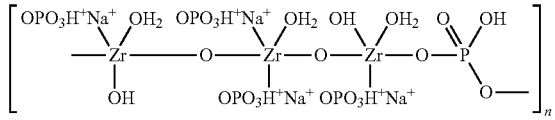

As shown, the material contains both H$^+$ and Na$^+$ as counter-ions, which are responsible for ion exchange. The relative content of these ions can be controlled by the pH to which acid ZrP (or H$^+$ZrP) is titrated with NaOH. The composition of the resultant product of titration, Na$_x^+$H$_{2-x}^+$ZrP (or abbreviated as "NaHZrP" herein), may vary during ion exchange processes in dialyate. The hydrous zirconium oxide (HZO) containing acetate (HZO.Ac) as a counter ion serves as an anion exchanger to remove phosphate. The material also prevents leaching of phosphate from NaHZrP and removes anions (e.g., fluoride) in water that may cause harm to a patient during dialysis. The acetate released during ion exchange is also a base to correct for acidosis by acetate metabolism. The compositional formula of hydrous zirconium oxide (HZO) can be ZrO$_2$.nH$_2$O (i.e. zirconium oxide hydrate) or ZrO$_2$.nOH . . . H$^+$An$^-$ in the anion form wherein An is an anion attached to HZO, such as acetate ("Ac"), chloride, etc. Without the anion, it can be considered as partially oxalated zirconium hydroxide with various degrees of $O^{2-}$, $OH^-$ and $H_2O$ bonded to Zr, i.e., $Zr(OH)_xO_y(H_2O)_z$. The granular activated carbon in the cartridge is used in the REDY cartridge for the removal of creatinine, uric acid, and nitrogenous metabolic waste of the patient as well as chlorine and chloramine from water. Thus the REDY regenerative dialysis system is efficient to provide both safety and simplicity of water treatment and hence convenience for hemodialysis. The efficacy and safety record of the system has been well established.

Potable tap water in 6 liter volumes and prescribed amounts of sodium chloride, sodium bicarbonate, and dextrose have been used to create the initial (precursor) dialysate solution for sorbent dialysis. The preparation of the precursor dialysate solution can involve dissolving and mixing the electrolytes and sugar with tap water in large jugs, for example, in a 6-liter jug. The measuring and mixing involved can be prone to error. Before passing through the dialyzer during prime, the precursor dialysate solution is passed through the sorbent cartridge for purification. As it flows through the sorbent cartridge, impurities such as bacteria, pyrogens, endotoxins, metals, and organic solutes are removed from the precursor dialysate solution. The purified dialysate is stored in a dialysate reservoir until it is circulated to the dialyzer. Once it leaves the dialyzer, the used (spent) dialysate, which includes a patient's ultrafiltrate fluid, passes through the sorbent cartridge, for conversion into regenerated dialysate, also known as cartridge effluent. As indicated, zirconium phosphate present in the sorbent cartridge also serves as a cation exchanger to remove $Ca^+$, $Mg^+$, $K^+$, and other cations in dialysate. An infusate system adds calcium, magnesium, and potassium electrolytes to the regenerated dialysate, thus allowing a balance of electrolyte level in the patient's blood (Ca, Mg, K) to be maintained as well as providing safety for dialysis treatment with regard to water quality. The regenerated dialysate then flows back into a dialysate reservoir, ready to be sent to the dialyzer. In a conventional "6-liter" system, the waste dialysate that must be disposed of after a dialysis treatment can significantly exceed six liters in volume.

A dialysis system that uses less volume of dialysate, eliminates bicarbonate requirements in the precursor dialysate (priming) solution to reduce ingredient amounts, preparation steps and formulation complexity, uses smaller scale components for increased portability and convenience, produces less waste, and/or that can be easily and cost-effectively resupplied, while maintaining purity standards, would be desirable.

SUMMARY OF THE INVENTION

A feature of the present invention is to provide a method for treating dialysate solutions used in dialysis systems which can meet one or more of the above desired needs.

A further feature of the present invention is to provide method for treating post-sorbent dialysate during an initial dialysis time period, which provides bicarbonate in a physiological range in the regenerated dialysate while eliminating the need for priming the sorbent system with bicarbonate-containing solution and/or inclusion of a bicarbonate layer in the sorbent cartridge.

A further feature of the present invention is to provide a method for treating post-sorbent dialysate nearer to the end of a dialysis treatment, which provides reduction of sodium levels in the regenerated dialysate to a physiological range using dilution fluid without burdening the system with excessively large volumes of additional fluids for handling and disposal.

A further feature of the present invention is to provide a system which can carry out the indicated methods of the present invention.

A further feature of the present invention is to provide a computerized method for pre-evaluating and classifying dialysis patients to provide more customized dialysis treatments for them through the sorbent system.

A further feature of the present invention is to provide a computer program product which can be used to implement such a computerized method for selection and management of dialysis treatments for patients.

Additional features and advantages of the present invention will be set forth in part in the description which follows, and in part will be apparent from the description, or may be learned by practice of the present invention. The objectives and other advantages of the present invention will be realized and obtained by means of the elements and combinations particularly pointed out in the written description and appended claims.

To achieve these and other advantages and in accordance with the purposes of the present invention, the present invention relates to a method of treating dialysate comprising a) passing spent dialysate received from a dialyzer through a sorbent cartridge to produce regenerated dialysate that is discharged from the sorbent cartridge for circulation back to the dialyzer; b) introducing bicarbonate solution into the regenerated dialysate during a first dialysis treatment time period to provide a treated regenerated dialysate that is circulated to the dialyzer; c) adding sterile water to the regenerated dialysate during a second dialysis treatment time period occurring after the first dialysis treatment time period to provide a diluted regenerated dialysate that is circulated to the dialyzer.

The present invention further relates to a dialysis system for carrying out the indicated method. The dialysis system can comprise a dialyzer having a blood flow path, a dialysate flow path, a dialysate inlet for receiving fresh or regenerated dialysate into the dialyzer, and a dialysate outlet for discharging spent (used) dialysate from the dialyzer; a sorbent cartridge configured for regenerating spent dialysate, wherein the sorbent cartridge comprises a sorbent cartridge inlet and a sorbent cartridge outlet, a fluid circuit comprising a first fluid passageway configured to provide fluid communication between the dialysate outlet of the dialyzer and the sorbent cartridge inlet, and a second fluid passageway configured to provide fluid communication between the sorbent cartridge outlet and the dialysate inlet of the dialyzer; a source of bicarbonate solution which is fluidly coupled to the second fluid passageway; a pump for delivery of the bicarbonate solution at a controlled rate from the source of bicarbonate solution into the second fluid passageway; and a supply of sterile water which is fluidly coupled to the second fluid passageway for introducing sterile water into the second fluid passageway from the supply container of sterile water.

The present invention further relates to a kit comprising a first package, a second package and third package. The first package contains a dialyzer comprising a blood flow path, a dialysate flow path, and a dialysate inlet and a dialysate outlet both in fluid communication with the dialysate flow path, a sorbent cartridge configured for regenerating used dialysate, the sorbent cartridge comprising a sorbent cartridge inlet and a sorbent cartridge outlet, a first tubing configured to provide a fluid communication between the dialysate outlet of the dialyzer and the sorbent cartridge inlet, an expandable reservoir comprising a reservoir inlet and a reservoir outlet, a second tubing configured to provide a fluid communication between the sorbent cartridge outlet and the reservoir inlet, and a third tubing configured to provide a fluid communication between the reservoir outlet and the dialysate inlet of the dialyzer. The second package contains a supply container containing from about 1.5 liters to about 2.0 liters of sterile water, first primary tube, an orifice flow controller, and a second primary tube, wherein the first primary tube is configured to fluidly connect the sterile water supply container and the orifice flow controller, and the second primary tube is configured to connect the venture constrictor with the second tubing. The third package contains a supply container comprising a container containing pumpable concentrated bicarbonate solution or a container containing dry bicarbonate powder wherein the container has a water inlet which allows entry of purified water and an outlet from which concentrated bicarbonate solution exits, and first bicarbonate carrying tubing for delivery of the concentrated bicarbonate solution to a pump or orifice flow controller and/or second bicarbonate carrying tubing for delivery of the concentrated bicarbonate solution from the pump or orifice flow controller to the third tubing, and optionally an orifice flow controller.

The present invention further relates to a method for pre-evaluating dialysis patients as part of treatments thereof, comprising a) inputting dialysis patient data into a central processing unit (CPU), wherein the patient data comprises, for example, urea donation data during dialysis treatment(s), body mass data, sodium serum data during dialysis treatment(s), and patient blood chemistry data, obtained from medical and/or dialysis treatment records of the patient; b) storing the patient data in the CPU; c) evaluating a dialysis patient prior to initiating a dialysis treatment session for the patient, comprising i) retrieving the patient data from the CPU, ii) determining 1) if the patient requires introduction of bicarbonate solution into regenerated dialysate during a first dialysis treatment time period to provide a treated regenerated dialysate that is circulated to the dialyzer and if so, further computing the introduction timing and rate needed thereof, and 2) if the patient requires addition of sterile water to the regenerated dialysate during a second dialysis treatment time period occurring after the first dialysis treatment time period to provide a diluted regenerated dialysate that is circulated to the dialyzer and if so, further computing the introduction timing and rate needed thereof; and d) performing dialysis on the patient using any bicarbonate solution and/or sterile water introduction timing and rate computed in step c).

The present invention further relates to a system for pre-evaluating dialysis patients as part of treatments thereof, comprising a computer comprising at least one memory device and at least one processor, wherein the at least one memory device is configured to have patient data inputted and stored therein, wherein the patient data comprises, for example, urea donation data from dialysis treatment(s), body mass data, sodium serum data from dialysis treatment(s), and patient blood chemistry data, obtained from medical and/or dialysis treatment records of the patient; the at least one processor operable for executing a computer program capable of performing computations based on retrieved patient data from the at least one memory device, wherein the computations determining 1) if the patient requires introduction of bicarbonate solution into regenerated dialysate during a first dialysis treatment time period to provide a treated regenerated dialysate that is circulated to the dialyzer and if so, further computing the introduction timing and rate needed thereof, and 2) if the patient requires addition of sterile dilution water to the regenerated dialysate during a second dialysis treatment time period occurring after the first dialysis treatment time period to provide a diluted regenerated dialysate that is circulated to the dialyzer and if so, further computing the introduction timing and rate needed thereof.

The present invention further relates to a non-transitory computer readable medium with a computer program product embodied thereon, wherein when the computer program product is performed on a processor in a computerized device provides a method for performing computations of one or more or all of the indicated steps of the indicated pre-evaluation based method.

It is to be understood that both the foregoing general description and the following detailed description are exemplary and explanatory only and are intended to provide a further explanation of the present invention, as claimed.

The accompanying drawings, which are incorporated in and constitute a part of this application, illustrate several embodiments of the present invention and together with the description, serve to explain the principles of the present invention.

DETAILED DESCRIPTION OF THE INVENTION

Figure 1:
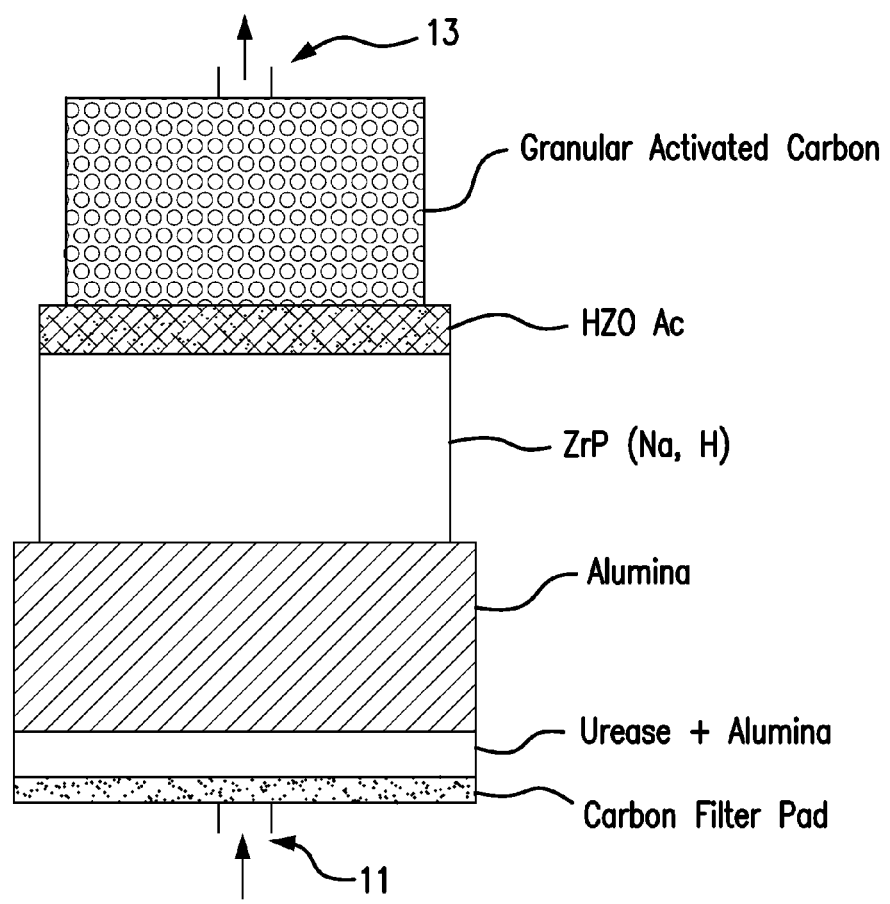
FIG. 1 is a schematic diagram showing a REDY® cartridge.

The present invention relates to treating dialysate solutions used in dialysis, which can provide more efficient and reduced use of dialysate fluids, electrolytes, sorbent cartridge materials, equipment scale, or any combinations of these, while maintaining purity standards and applicable physiological ranges for bicarbonate, sodium, and other dialysate solution components over the course of a dialysis treatment session. Dialysate can be treated in an early part of a dialysis treatment session by external infusion of bicarbonate solution into the dialysate circuit to provide a physiological level of bicarbonate and eliminate the need for bicarbonate requirements in concentrates used for preparation of precursor dialysate (priming) solutions and/or include solid bicarbonate layer in a sorbent cartridge. Dialysate can be treated in a latter part of a dialysis treatment session by introduction of sterile dilution water to reduce sodium concentration to physiological level in the dialysate. For purposes herein, the term "treating," as used in relation to a dialysate solution, refers to modifying the composition of the dialysate solution, such as by changing the concentration of one or more components originally present or absent therefrom, such as by adding, removing, and/or transforming one or more components in the dialysate solution. The treating of the dialysate solution can encompass not only purifying or regenerating dialysate by action of a sorbent cartridge, but also a modification made to the composition of the dialysate in the dialysate fluid circuit outside the sorbent cartridge. The present invention is useful in treating dialysate fluids, such as used in hemodialysis (HD) and peritoneal dialysis (PD), or other dialysis methods. For purposes of the present invention, a dialysis solution can mean dialysate fluids that are useful in hemodialysis or sorbent dialysis systems or a peritoneal dialysis solution.

The present invention provides a method for treating regenerated dialysate during an initial time period of a dialysis treatment session which provides bicarbonate levels in a physiological range using a controlled rate infusion into the regenerated dialysate. This can eliminate the need to include bicarbonate in a precursor dialysate solution used for priming the sorbent dialysis system and/or the inclusion of a bicarbonate layer in the sorbent cartridge. This simplifies the formulation of the precursor dialysate solution and reduces the risk of mixing errors. Precursor dialysate solutions have been used which are based on combinations of bicarbonate and other components, such as dextrose or other sugar (e.g., as an osmotic agent), sodium chloride, and any other electrolytes or acidifiers. The bicarbonate content used in such precursor dialysate solutions that include bicarbonate is significantly reduced upon a single passage through the sorbent cartridge. In view of this, it can be difficult to estimate bicarbonate amounts needed in a precursor dialysate solution that will yield a physiological level targeted in the regenerated dialysate that will be fed to the dialyzer during a dialysis treatment session. It has been found that up to about 90 wt % or more of bicarbonate used in the preparation of a precursor dialysate solution containing bicarbonate, dextrose and sodium chloride used to prime the sorbent system can be decomposed upon the first pass through the sorbent cartridge, leaving only about 10 wt % or less of the original amount of bicarbonate left in the regenerated dialysate that is fed to the dialyzer. If 30 mEq/L of bicarbonate is targeted for the regenerated dialysate, this bicarbonate loss rate to the sorbent column would necessitate a bicarbonate concentration of about 300 mEq/L in a precursor dialysate solution that is fed to the sorbent cartridge. This means that a large excess amount of bicarbonate will be needed in the precursor dialysate solution used for priming. In the present invention, the infusion of bicarbonate into the regenerated dialysate fluid in the initial period of a dialysis treatment at a controlled rate avoids the shortcomings of such a low efficiency delivery strategy for bicarbonate. The infusion of the bicarbonate is referred to herein as "external" as the bicarbonate is introduced from preformed supply outside the dialysate circuit and is not generated in situ as a byproduct of the interaction of spent dialysate with contents of a sorbent cartridge.

For a sorbent cartridge which comprises at least one urease-containing layer, at least one zirconium phosphate-containing layer, and at least one zirconium oxide-containing layer, the carbonate from the urea hydrolysis in the sorbent cartridge combines with the hydrogen ions in zirconium phosphate in the sorbent cartridge to form bicarbonate in situ. In a method of the present invention, this in situ generation of bicarbonate occurs concurrent with the externally-sourced infusion of bicarbonate into the regenerated dialysate during an initial time period of the dialysis treatment. Bicarbonate generated in situ in the sorbent column is included in the regenerated dialysate solution that is discharged from the sorbent cartridge. The bicarbonate concentration in the regenerated dialysate effluent from the sorbent cartridge is dependent on the amount of urea nitrogen exchanged for hydrogen in the sorbent column. A gradual upswing in the bicarbonate concentration in the regenerated dialysate occurs during the course of a dialysis treatment as more hydrogen ions are neutralized in the zirconium phosphate layer. The initial amount of bicarbonate generated in situ in the sorbent column usually is very low for most patients, approaching zero, and then it will tend to steadily climb as a function of time as the dialysis treatment session continues and progresses. Bicarbonate that remains in spent dialysate usually will be mostly or entirely picked up by the sorbent cartridge in the spent dialysate's next pass or next several passes through the sorbent cartridge. In view of this, the sorbent column's output of in situ generated bicarbonate can steadily increase in individual successive fluid cycles over the course of a dialysis treatment session, and not as an accumulation of bicarbonate combined over multiple fluid cycles of the dialysate through the sorbent system. Eventually, bicarbonate concentration in the regenerated dialysate exiting the sorbent cartridge approaches or reaches a target value for the patient at which the externally-sourced infusion of bicarbonate is no longer needed. The external infusion of the bicarbonate can be discontinued shortly before, at the same time, or shortly after such a time. If the bicarbonate concentration in the regenerated dialysate before infusion of a bicarbonate solution therein is lower than the concentration of bicarbonate in the infusate, the bicarbonate level in the regenerated dialysate can drop after external bicarbonate infusion is discontinued. A tolerable range of bicarbonate concentration can encompass a range of values for a given patient that may be broader than the prescribed physiological range, provided that the exposure time is short enough to avoid safety concerns. Preferably, the switchover is coordinated such that the bicarbonate concentration in the regenerated dialysate remains in a physiological acceptable range during the transition period from external bicarbonate infusion to reliance on levels of bicarbonate generated in situ by the sorbent system during the dialysis treatment session. The external bicarbonate infusion may be discontinued before the in situ-generated bicarbonate levels have reached a target value, and the bicarbonate concentration in the regenerated dialysate may drop in the interim until it reaches the target. This condition can be acceptable provided that the target value of bicarbonate is acquired as the dialysis treatment session continues within a time period such that the dialyzer system does not operate with a low bicarbonate level for the patient for an unsafe period of time. The timing of the discontinuance of the external bicarbonate infusion can be coordinated with the level and rate of in-situ generation of bicarbonate in the sorbent system.

The indicated infusion of bicarbonate in the regenerated dialysate can eliminate in part or completely the need for including a solid bicarbonate layer in the sorbent cartridge, such as near the discharge end of a sorbent cartridge, as a means to contribute bicarbonate to the regenerated dialysate. A solid (particulate) bicarbonate layer, if arranged near the discharge end of a sorbent cartridge, gradually dissolves into the dialysate solution passing through the layer and is carried out with the regenerated dialysate discharged from the sorbent cartridge. A solid bicarbonate layer used in the sorbent cartridge in such a manner can reduce the amount of bicarbonate needed in a precursor dialysate solution. As with other residual bicarbonate in spent dialysate from other sources, dissolved bicarbonate from the solid bicarbonate layer that remains in spent dialysate will be mostly or entirely picked up by the sorbent cartridge in the spent dialysate's next pass or next several passes through the sorbent cartridge. The inclusion of a solid bicarbonate layer in the sorbent cartridge adds cost and complexity to the device, and can continue to add bicarbonate to the regenerated dialysate without being controllable throughout the dialysis treatment session, including during treatment times when possibly not needed or wanted.

Figure 3:
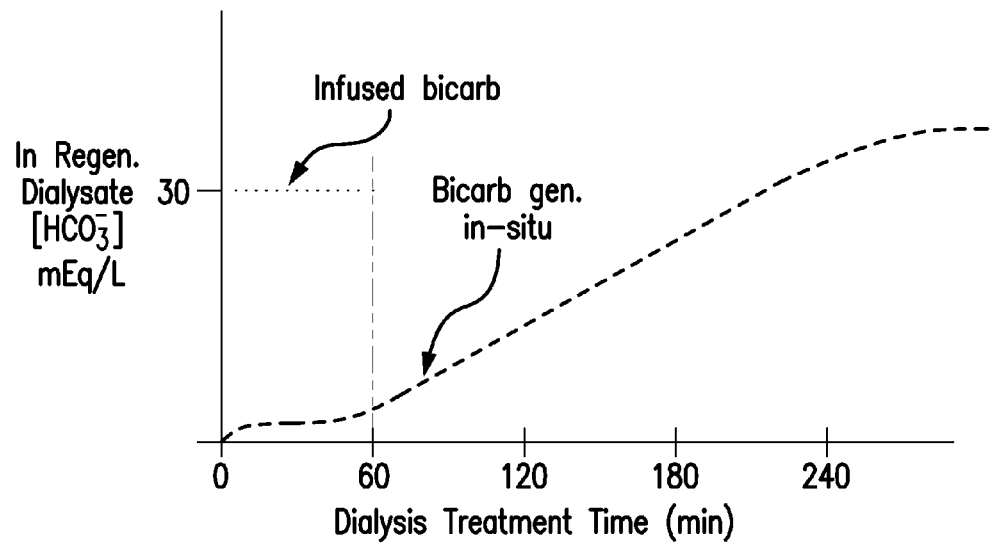
FIG. 3 is a plot that shows bicarbonate concentrations ([$HCO_3^-$], as mEq/L) in regenerated dialysate before and after infusing bicarbonate with respect to dialysis treatment time (in minutes), in accordance with an example of the present application.

The plot in FIG. 3 shows bicarbonate concentrations ($[HCO_3^-]$, as mEq/L) in regenerated dialysate before and after infusing bicarbonate solution with respect to dialysis treatment time. Bicarbonate levels used in dialysis solutions commonly are set slightly higher than normal blood levels to encourage diffusion of bicarbonate into the blood and to act as a pH buffer to neutralize the metabolic acidosis that is often present in these patients. Patients on dialysis lack kidney function so neutralizing the accumulating acids has to happen during dialysis. Normal concentration of bicarbonate in the body may be in the range of 20 to 29 mEq/L, or other values depending on the particular patient. FIG. 3 shows infusion of the bicarbonate solution for the first 60 minutes of the dialysis treatment time for sake of illustration, and other time periods can be used. During the bicarbonate infusion period of time used in the illustration in FIG. 3, the bicarbonate concentration in the regenerated dialysate is kept at about 30 mEq/L throughout that time period. As used herein, "mEq/L" refers to the concentration of a particular dialysate component (solute) present in proportion to the amount of water present. More specifically, mEq/L refers to the number of milli-equivalents of solute per liter of water. Milli-equivalents per liter are calculated by multiplying the moles per liter of solute by the number of charged species (groups) per molecule of solute, which is then multiplied by a factor of 1,000. The 30 meq/L bicarbonate concentration is used for illustration, and other bicarbonate concentrations may be prescribed and used, depending on the patient. As indicated in the plots in FIG. 3, if the bicarbonate infusion is not used, then the bicarbonate concentration in the regenerated dialysate will be approximately zero mEq/L when the dialysis treatment starts and will gradually progressively climb from the initial small values as greater levels of bicarbonate is generated in situ from the activity of the sorbent cartridge on spent dialysate. A sorbent cartridge which comprises at least one urease-containing layer, at least one zirconium phosphate-containing layer, and at least one zirconium oxide-containing layer, can be expected to interact with urea in spent dialysate and generate bicarbonate in situ to lead to such a discharge profile over the course of a dialysis session. Though the sorbent cartridge used for this illustration includes urease, zirconium phosphate, and zirconium oxide, the method of the invention can be applicable to other sorbent cartridge designs which have similar discharge profiles with respect to bicarbonate during the course of a dialysis treatment. To simplify the illustration, bicarbonate from the conversion of acetate in a patient's liver from any acetate included in any acid concentrate used in the formulation of the precursor dialysate is not counted as part of the bicarbonate concentration that the dialyzer receives, but could be counted towards the total value if present and can be estimated.

The method of the present invention can maintain bicarbonate concentrations in the regenerated dialysate that are at safe or physiological levels for at least the initial infusion period, and until levels of bicarbonate generated in situ by sorbent cartridge activity can build to an acceptable level or are near/approaching that level. The introducing of the bicarbonate solution into the regenerated dialysate during the first dialysis treatment time period can be at a rate to provide treated regenerated dialysate with a bicarbonate concentration in a range of 20-40 mEq/L, or 22-39 mEq/L, or 25-35 mEq/L, or 28-32 mEq/L, or other values. The bicarbonate concentration in the regenerated dialysate can be kept within a tolerance range relative to a target value, such as 30±1 mEq/L, or 30±2 mEq/L, 30±3 mEq/L, 30±4 mEq/L, or 30±5 mEq/L, or other values during the bicarbonate infusion time period. The bicarbonate concentration in the regenerated dialysate can be kept within any of the indicated target values with tolerance or other target values with tolerances for at least 90%, or at least 95%, or at least 99%, or 100% of the entire time period within which bicarbonate solution is infused into the regenerated dialysate. Since the bicarbonate concentration in the regenerated dialysate discharged from the sorbent cartridge in an initial portion of dialysis treatment (e.g., the first 120 minutes, or 90 minutes, or 60 minutes, or 30 minutes) will be zero or remain very low (so can be assumed to be zero), mass balances can be used to calculate an infusion flow rate needed for a bicarbonate solution (with a predetermined bicarbonate concentration) into the regenerated dialysate having a known flow rate (e.g., from a flow meter) to provide a treated regenerated dialysate having the target concentration of bicarbonate (before it reaches the dialyzer). A source of the bicarbonate solution can be fluid connected to the dialysate fluid circuit (post sorbent) via tubing, and a pump or other fluid advancement mechanism, such as a programmable syringe pump, or an orifice flow controller, can be used to provide the desired infusion rate for the bicarbonate solution. The bicarbonate solution can be saturated with bicarbonate or contain less than saturated concentrations. More dilute solutions of bicarbonate may be used with the understanding that increased volumes of fluids will need to be processed and handled by the system for disposal. Preferably, smaller volumes of the working fluids, such as the bicarbonate source and sterile dilution water, are used. The bicarbonate can be a bicarbonate salt, such as an alkali metal bicarbonate, e.g., sodium bicarbonate. The bicarbonate can be a single kind of bicarbonate salt or a combination of different kinds of bicarbonate salts. A bicarbonate concentrate containing sterile water at saturated or near-saturated levels of sodium bicarbonate can be used, or other concentrations can be used as indicated.

A method of the present invention can include a post-sorbent bicarbonate infusion into dialysate during an initial or first dialysis treatment time period, such as occurring within an initial 50%, or 45%, or 40%, or 30%, or 25%, or 20%, or 15%, or 10%, or within other times, of total dialysis treatment time of a dialysis treatment session. As used herein, the term "post-sorbent" refers to introduction of an indicated component into dialysate solution in any portion of the dialysate fluid circuit after the outlet of the sorbent cartridge and before the inlet of the dialyzer. If a dialysis treatment session runs for 240 minutes (4 hours), as an illustration, then the post-sorbent bicarbonate infusion can be implemented during the initial 120 minutes (i.e., zero time to 120 minutes thereafter), or 96 minutes, or 72 minutes, or 60 minutes, or 48 minutes, or 36 minutes, of the dialysis treatment session or other initial time periods. The post-sorbent bicarbonate infusion time period can comprise 10% to 45%, or 12.5% to 42.5%, or 15% to 40%, or 20% to 37.5%, or 25% to 35%, or other percentages, of the total dialysis treatment time of a dialysis treatment session.

Sodium levels in dialysate of some patients can increase to unsafe or undesired levels in the latter part of a dialysis treatment session. A narrow range of patients may have low enough urea to reduce the dilution volume needed to control sodium concentration in the dialysate. Many other patients, however, need help during a dialysis treatment session in lowering sodium in the regenerated dialysate to safe levels. Another feature of the present invention provides a method for treating regenerated dialysate in the latter part of a dialysis treatment, which uses sterile dilution fluid to provide reduction of sodium levels in the regenerated dialysate to a physiological range. As indicated, urea is converted to ammonia in the presence of urease in the sorbent cartridge, which is then removed by the zirconium phosphate in exchange for the hydrogen ions and sodium ions ($Na^+$). Throughout a dialysis treatment, the dialysate sodium concentration begins lower than the patient's serum level and increases to a level that is higher than the patient's sodium in many patients, if no action is taken. The range in sodium concentration is a result of mass transfer between the dialysate, the sorbent column, and the patient. In view of this, the sodium ions carried in the regenerated dialysate discharged from the sorbent cartridge tend to progressively increase in amount in the dialysate over the dialysate treatment session. In a feature of the present invention, the sodium ion concentration, such as expressed in units of mEq/unit volume dialysate, in the regenerated dialysate can be reduced by introduction of sterile water into the sorbent system post-sorbent at a controlled rate to effectively lower (by dilution) the sodium concentration in the regenerated dialysate within a physiological range for recirculation to the dialyzer. This approach can be implemented without burdening the system with very large volumes of additional fluids for handling and disposal. The sorbent generation of sodium can be independent of the dilution level in the spent dialysate. The activity of the sorbent column in the sorbent cartridge is generally insensitive to the level of dilution of sodium in the spent dialysate that is fed to the sorbent cartridge. In view of this, dilution of the dialysate can be used to directly manage the sodium level therein without adversely impacting or altering the sorbent cartridge functions.

Figure 4:
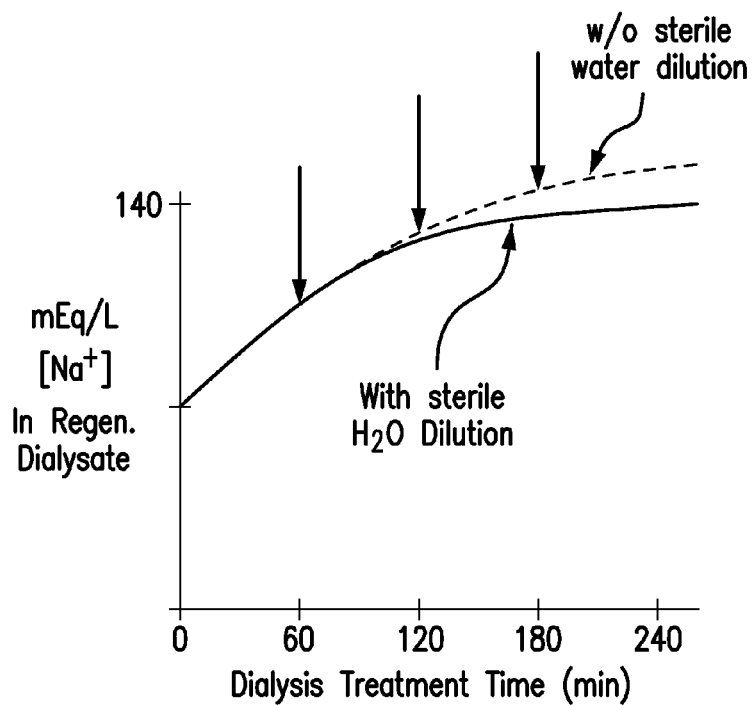
FIG. 4 is a plot that shows sodium ion concentrations ([$Na^+$], as mEq/L) in regenerated dialysate with and without introducing sterile dilution water with respect to dialysis treatment time (in minutes), in accordance with an example of the present application.

FIG. 4 is a plot that shows sodium ion concentrations ($[Na^+]$, as mEq/L) in regenerated dialysate with and without introducing sterile dilution water with respect to dialysis treatment. This illustration shows that the introduction of sterile water in the final 120 minutes of the dialysis treatment to dilute the regenerated dialysate effectively lowered the sodium concentration to below 140 mEq/L, whereas the sodium concentration would reach values higher than 140 mEq/L without the sterile water dilution. Other time periods can be used for the sterile dilution water introduction, and the 140 mEq/L concentration is used for sake of illustration, as other upper limit values may be prescribed (e.g., 145 mEq/L, 150 mEq/L, and so forth), depending on the patient. The sodium concentration in the regenerated dialysate discharged from the sorbent cartridge can be monitored during a dialysis treatment (e.g., the final 120 minutes, or 90 minutes, or 60 minutes, or 30 minutes, or other final time periods). This can be done based on predictions or profiles determined from historical clinical treatments performed on the patient (or class of patient), or by using a conductivity meter arranged downstream of the sorbent cartridge to actively monitor the regenerated dialysate during a dialysis treatment after it leaves the sorbent cartridge and before or after reaching the location in the dialysate fluid circuit where sterile water dilution is configured to be made. A conductivity meter, if used, can estimate, based on the conductivity of the fluid passing therethrough, the concentration of sodium within the fluid. Sterile dilution water can be added to the regenerated dialysate if the conductivity reading indicates that the sodium level in the regenerated dialysate is higher than desired. In view of this option and since the sodium content of the sterile dilution water is zero, mass balances can be used to calculate an introduction flow rate needed for the sterile dilution water into the regenerated dialysate having a known flow rate (e.g., measured using a flow meter) to meet a target value for the sodium concentration in the diluted regenerated dialysate.

A method of the present invention can include a post-sorbent sterile dilution water introduction to reduce sodium levels in the regenerated dialysate in a later or second dialysis treatment time period, such as occurring within a final 50%, or 40%, or 30%, or 25%, or 20%, or 15% of the total dialysis treatment time of the same dialysis treatment session. The introducing of the sterile dilution water into the regenerated dialysate during the second dialysis treatment time period can be at a rate to provide treated regenerated dialysate with a sodium concentration in a range of 120-150 mEq/L, or 121-149 mEq/L, or 125-145 mEq/L, or 130 to 140 mEq/L, or other values. The sodium concentration in the regenerated dialysate can be reduced to any of the indicated concentration ranges within 30 minutes, or within 15 minutes, or within 10 minutes, or within 5 minutes, or within other times. If a dialysis treatment session runs for 240 minutes (4 hours), as an illustration, then the post-sorbent introduction of sterile dilution water to reduce sodium levels can be implemented during the final 120 minutes, or 96 minutes, or 72 minutes, or 60 minutes, or 48 minutes, or 36 minutes, of the dialysis treatment session or other final time periods. The post-sorbent sodium infusion time period can comprise 10% to 45%, or 15% to 40%, or 20% to 35%, or other percentages, of the total dialysis treatment time of a dialysis treatment session. The sterile dilution water addition to the regenerated dialysate can keep sodium concentration in the regenerated dialysate within any of the indicated target range values or other target range values (or below the upper limit of the target range) for at least 90%, or at least 95%, or at least 99%, or 100% of the entire time period within which sterile dilution water is added into the regenerated dialysate.

Sterile water or purified water that is used in the sorbent system of the present invention is pretreated or treated in order that it is essentially pyrogen-free (i.e., is sterile) and at least meets the purity requirements established by the Association for the Advancement of Medical Instrumentation (AAMI) for dialysate compositions. The water may also be referred to as treated water or AAMI-quality water. A monograph describing water treatment for dialysate, monitoring of water treatment systems, and regulation of water treatment systems is available from AAMI (Standards Collection, Volume 3, Dialysis, Section 3.2 Water Quality for Dialysis, 3 ed., 1998, AAMI, 3330 Washington Boulevard, Arlington, Va. 22201) or through the Internet at http://www.aami.com.

Both or only one of the indicated post-sorbent bicarbonate infusion and post-sorbent sterile dilution water introduction to reduce sodium can be used in the same dialysis treatment session for a patient, such as depending on the needs and treatment profile of the particular patient. If both are used, there can be an intervening time period during the dialysis treatment session when neither the post-sorbent bicarbonate infusion or the post-sorbent introduction of sterile dilution water is being implemented.

A source of the sterile dilution water can be provided using a supply of sterile water which is fluidly coupled to the dialysate fluid circuit (post sorbent). The supply of sterile water can comprise a bag or other container suitable for filling with and holding sterile water. The bag or other container can be flexible or rigid in construction. The bag or other container can be polymer material in thin layer or sheet form. The supply of sterile water can be a flexible bag that is hung or otherwise held in position at a raised position relative to the dialysate fluid circuit for gravity feeding of the sterile water into a fluid passageway coupled with the dialysate fluid circuit. A bag or other container used to store the sterile water can be geometrically shaped, such as funnel-shaped at least at its bottom portion. This permits smaller volumes of fluid to be used in the bag that provide an adequate hydrostatic pressure and fluid seal at the fluid outlet of the bag. The supply of sterile water can comprise a container having a volume of sterile water of about 2.0 liters or less, or other volumes. According to Bernoulli's principle, the pressure in a tube is inversely proportional to flow rate. When a sterile dilution water bag or other container hung from a stand or the like for gravitational flow is fluidly coupled to the dialysate fluid circuit through which regenerated dialysate flows, flow of the regenerated dialysate in the dialysate fluid circuit creates a pressure differential with respect to the sterile water stored in the sterile dilution water bag or other container. This induces flow of the sterile water from the bag into the dialysate fluid circuit through an intervening tubing system.

Control of the flow rate of the sterile dilution water from the supply bag to the dialysate fluid circuit under these conditions can be provided with an intervening tubing system that includes an orifice flow controller. As used herein, the term "orifice flow controller" refers to a mechanism or structure that has a body that defines an orifice or flow passageway through which fluid flows from tubing fluidly coupled at an inlet of the orifice flow controller to tubing fluidly coupled at the outlet of the orifice flow controller. The orifice can be designed to have a smaller diameter than the tubings at its inlet and outlet to effectively impose flow rate control over fluid passing from one of the tubes to the other. A constant or substantially constant predetermined flow rate can be provided by the orifice flow controller. In such a manner, flow of regenerated dialysate through the fluid circuit can create a fluid pressure differential relative to the supply of sterile water in the container to induce flow of sterile water from the supply of sterile water in the container through the tubing system into the fluid circuit at a controlled flow rate via the orifice flow controller. The orifice flow controller can be a component that defines a single orifice having a single diameter profile, or it can be a device having manual or automated capability for orifice diameter adjustment. The orifice flow controller can be a separate detachable discrete component with respect to both of the tubings, or it can be a structure that is integrally formed or permanently attached at a distal end of one of the pieces of tubing.

The addition of the sterile dilution water, such as a total added amount of 2.0 liters or other volumes, increases the total volume of fluid in the dialysate circuit by a volume corresponding to the added volume of sterile water. A fluid reservoir can be provided and used in the post-sorbent portion of the dialysate fluid circuit to accommodate this added volume of fluid to the sorbent system. The reservoir can be an expandable reservoir, or an open reservoir of fixed size, which can receive fluid from the dialysate fluid circuit and release enough fluid back into the dialysate fluid circuit adequate to keep the fluid passageways of the fluid circuit filled with fluid. The expandable reservoir can be a flexible bag that is fluidly coupled in-line with the dialysate fluid circuit and capable of retaining enough fluid within the bag to maintain a fluid seal at the outlet thereof during a dialysis treatment and is capable of expanding to effectively increase its storage volume space to accommodate the volume of sterile dilution water added to the dialysate fluid circuit, and which can receive fluid from the dialysate fluid circuit and release enough fluid back into the dialysate fluid circuit to keep the fluid passageways of the fluid circuit filled with fluid. An expandable reservoir bag or other container used to accommodate the increased volume of fluid from sterile water dilution, can be geometrically shaped. The expandable reservoir bag can be shaped in such a manner that at least the bag has a geometric minimum. As indicated, this permits smaller volumes of fluid to be used in a flexible bag or other fluid container to maintain an adequate hydrostatic pressure and fluid seal at the fluid outlet of the bag or other container.

The dialysis system of the present invention can comprise a dialyzer, a sorbent cartridge, sterile water supply, orifice flow controller, bicarbonate solution supply, bicarbonate solution pumping device, an expandable reservoir, connective tubing, as basic components of a dialysate circuit. The components can be sized such that the entirety of the dialysis circuit can be operated using a total volume of dialysate of about 5 liters or less, for example, about 4.5 liters or less, or about 4 liters or less, or about 3 liters or less, or other volumes. For these total volumes of dialysate, the dialysis system can be configured to provide a dialysate flow rate of from 150 to 500 ml/minute, or from 175 to 475 ml/minute, or from 200 to 450 ml/minute, or other flow rates. The dialysis system can allow blood flow rates of from 100 to 600 ml/minute, or from 125 to 575 ml/minute, or from 150 to 550 ml/minute, or other flow rates.

Many of the components of sorbent system usable in a dialysis system of the present invention, particularly disposable components such tubings for fluids, the sorbent cartridge, bag(s) of sterile dilution water, and/or the orifice flow rater controller, can be provided in portable kit form, such as in a single kit that can be used for a single dialysis treatment session and disposed of thereafter.

A system in accordance with the present invention can employ any suitable dialyzer, for example, high-flux dialyzers or low-flux dialyzers. The system of the present invention can operate using precursor dialysate solution prepared with potable tap water, or ultrapure fluid (for example, supplied from a bag of sterile saline). The dialysate circuit generally includes no additional filters capable of purifying water between the sorbent cartridge and the dialyzer where the dialysate contacts the patient's blood. The treatment can use tap water or lower quality or low purity water that can be filtered, cleaned, or run through a sorbent cartridge before a dialysis treatment to provide purified water (e.g., AAMI water). By permitting the use of tap water, the amount of pre-packaged purified water used for priming the system can be reduced or eliminated. Alternatively, ultrapure fluid and ultrapure dialysate can be made from the fluid which enables a dialysis treatment that uses pre-packaged sterile, sterilized, pure, or purified fluid, from the beginning. High-flux dialyzers can be used and enable the use of lower dialysate flow rates while maintaining treatment adequacy. The use of a low flow rate, although not required, does enable the systems of the present invention to run with lower volumes of dialysate compared to conventional 6-liters systems, making the shipment and resupply of ultrapure fluid both feasible and economical. The systems of the present invention can operate at higher volumes of dialysate fluids as well.

A dialysis system of the present invention which provides the indicated features can be configured wherein the supply of bicarbonate solution and the supply of sterile dilution water are automatically controllable for dispensing or they can be controlled non-automatically. A first tubing can be provided that is configured to provide a fluid communication between the dialysate outlet of a dialyzer and a sorbent cartridge inlet. A second tubing can be provided that is configured to provide a fluid communication between a sorbent cartridge outlet and an expandable reservoir inlet. A third tubing can be provided that is configured to provide a fluid communication between an expandable reservoir outlet and a dialysate inlet of the dialyzer. The first, second, and third tubings, together with the dialyzer, the sorbent cartridge, the expandable reservoir, and respective supplies of bicarbonate solution and sterile dilution water can be connected together to provide a dialysate circuit of the present invention. One or more dialysate pumps can be provided to circulate dialysate through the dialysate circuit. Pumps having chambers can be used. Peristaltic pumps can be used, for example, along one or more of the tubings of the dialysate circuit. One or more of the first, second, and third tubings can be arranged in the raceway of a peristaltic pump and the seated tubing and pump can be configured to move dialysate through the respective tubing and thus through the dialysate circuit. Where automatically controllable, the supply of bicarbonate solution and the supply of sterile dilution water can be automatically controlled at least in part based on signals provided to and/or from an electronic controller. The controlling can be based on whether the patient needs one or other of the bicarbonate solution and the sterile dilution water added to the dialysate at applicable respective time periods during the course of a dialysis treatment session. The determination of whether a patient is in need of one or other of the bicarbonate solution and the sterile dilution water added to the dialysate or not, can be based on pre-dialysis testing and/or prior patient history and/or using one or more pre-screening factors to determine expected needs of the patient. This pre-evaluation procedure can be computerized in part or completely, and can be integrated with a dialysis treatment that is performed on a screened patient. Controlling and determination of whether the patient needs one or other of the bicarbonate solution and the sterile dilution water added to the dialysate at applicable respective time periods during the course of a dialysis treatment session, can also be done by using sensors that are integrated into the system and which can provide real-time feedback to the system. Sensors that can be used in the system of the present invention include, for example, a conductivity sensor, urea sensor, or pH sensor, or a combination thereof.

Figure 5:
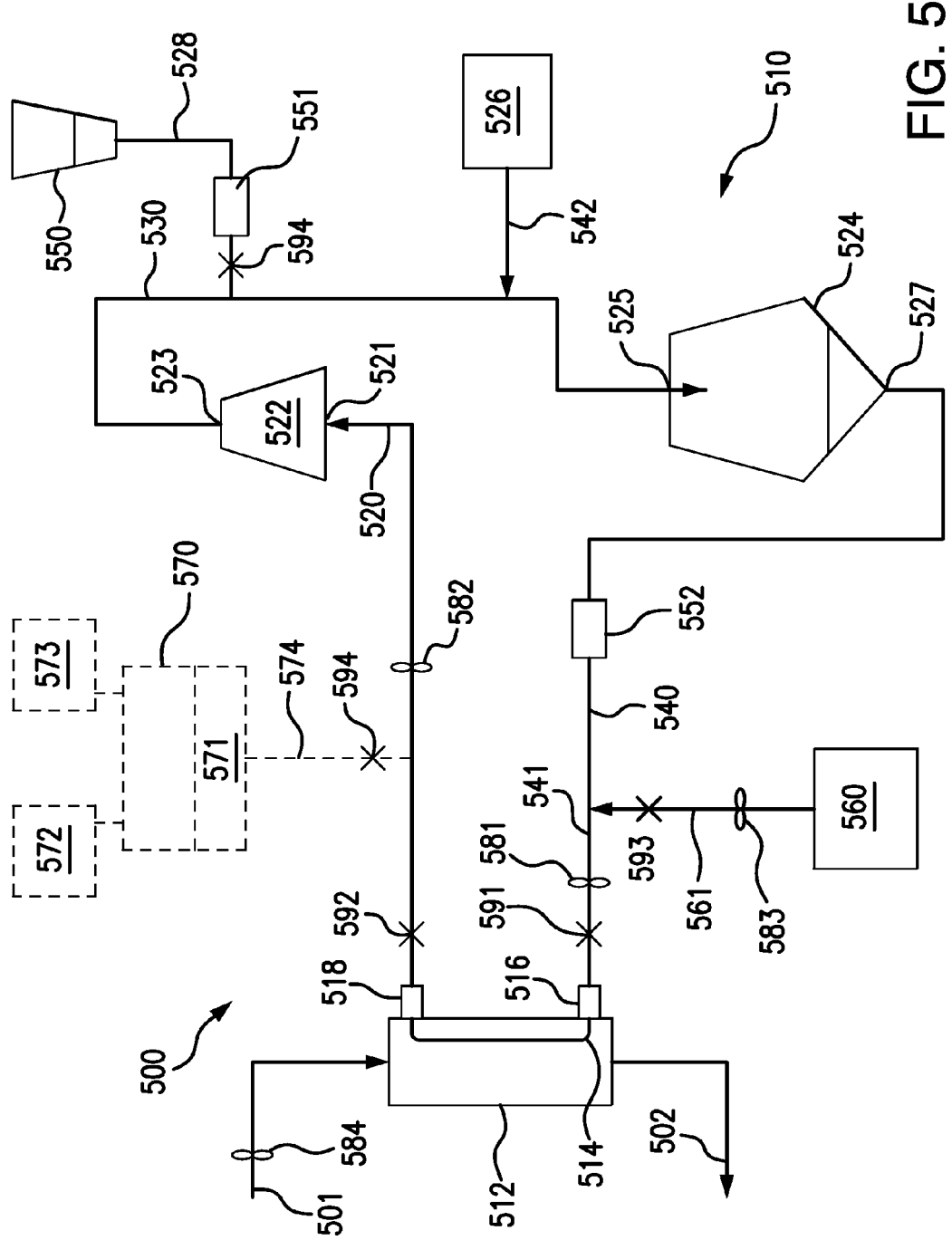
FIG. 5 is a schematic diagram of a dialysis system in accordance with an example of the present application.

With reference FIG. 5, a dialysis system 500 of the present invention can include a dialysate circuit 510 comprising a dialyzer 512, a sorbent cartridge 522, an expandable reservoir 524, sterile dilution water supply 550, orifice flow controller 551, bicarbonate solution source 560, precursor dialysate solution supply 570, and other components, such as fluid communications connecting these components and pumping and clamping/valving mechanisms, such as shown in FIG. 5. Dialyzer 512 includes a dialysate membrane that separates the interior of the dialyzer 512 into a blood side and a dialysate side. The dialysate side defines a dialysate flow path 514 that begins at a dialysate inlet 516 and ends at a dialysate outlet 518. Blood from the patient flows through the dialyzer 512 on the other side of the membrane (not shown), in the opposite direction to the flow direction of the dialysate 514, from blood inlet line 501 to blood outlet line 502 for return to the patient. A pump 584, e.g., a peristaltic pump, can be used to provide flow of the blood through the dialyzer 512. Both dialysate inlet 516 and dialysate outlet 518 are in fluid communication with dialysate flow path 514. Dialysate outlet 518 is in fluid communication with an inlet 521 to sorbent cartridge 522 by way of a tubing 520. The end of tubing 520 that enters sorbent cartridge inlet 521 is shown as an arrowhead to indicate a direction of flow of dialysate during a dialysis treatment. An outlet 523 of sorbent cartridge 522 is in fluid communication with a reservoir inlet 525 of expandable reservoir 524 by way of a tubing 530. The end of tubing 530 that intersects reservoir inlet 525 is shown as an arrowhead to denote the direction of dialysate flow during a dialysis treatment. Expandable reservoir 524 includes a reservoir outlet 527, at the bottom thereof. The reservoir outlet 527 is in fluid communication with tubing 540 into which bicarbonate solution is added from a bicarbonate solution source 560 to form treated regenerated dialysate 541 that flows through tubing 540 to dialysate inlet 516 of dialyzer 512. As indicated, the introduction of bicarbonate solution is provided during an initial time period of a dialysis treatment. Control of the addition of the bicarbonate solution into tubing 540 can be provided by a valve/clamp 593 and a pump or orifice flow controller 583 arranged in-line with tubing 561 that fluidly connects the bicarbonate solution supply 560 and tubing 540. When component 583 is a pump, the pump 583 used in the feeding of the bicarbonate solution from its source 560 to the tubing 540 can be a programmable syringe pump or other pumping device which can provide controlled flow rate pumping of small flow rates of fluid (e.g., from 1 to 100 ml/minute, or from 10 to 75 ml/minute, or from 20 to 50 ml/minute, or from 25 to 35 ml/minute, or other flow rates). An orifice flow controller can be used instead of a pump for component 583 for the feeding of the bicarbonate solution from its source 560 to the tubing 540 at a controlled rate, such as the flow rates indicated. Sterile water supply 550 is fluidly connected to tubing 530. As indicated, the introduction of sterile dilution water is provided during a later or final time period of a dialysis treatment when sodium concentration in the dialysate increases to or approaches an undesired level. Control of the addition of the sterile water into tubing 530 can be provided by a valve/clamp 594 arranged in-line with tubing 528 that fluidly connects the sterile water supply 550 and tubing 530. An orifice flow controller 551 also is arranged in-line with tubing 528 that fluidly connects the sterile water supply 550 and tubing 530. The orifice flow controller controls the flow rate of the sterile water from the sterile water supply 550 through tubing 528 to tubing 530 wherein it combines with regenerated dialysate. Each tubing 520, tubing 530, tubing 540, tubing 561, and tubing 528, can independently comprise a continuous length of tubing, two or more separate tubings that are connected together, or the like. Various connectors, valves, diverters, junctions, taps, septa, and inlets can be provided along, and/or as part of, the tubings. Pumps 581 and 582 can be used to provide flow of dialysate through the dialysate circuit 510, and specifically through spent dialysate tubing 520, regenerated dialysate tubings 530 and 540, and dialysate flow path 514 through dialyzer 512, such as shown in FIG. 5. An electrolytes supply container 526 can provide a supply of concentrated electrolyte solution (e.g., K, Ca, Mg solution) for addition during a dialysis treatment. Container 526 is in fluid communication with tubing 530 by way of a tubing 542. A pump, pump controller, and sensing or monitoring system (not shown) can be used to supply the concentrated solution of electrolytes from container 526 to dialysate circuit 510 in a manner that achieves and maintains a proper concentration of electrolytes in the dialysate circulating through dialysate circuit 510. Although the concentrated solution of electrolytes is shown being introduced to dialysate circuit 510 along tubing 530, it is to be understood that the electrolytes can be introduced to the regenerated dialysate in the dialysate circuit 510 at another location, for example, into tubing 540 and/or directly into expandable reservoir 524.

To initially prepare dialysate for circulation through dialysate circuit 510, the dialysate circuit 510 can be primed with a precursor dialysate solution 571 in supply container 570. The precursor dialysate solution can be prepared using a source of tap water 572 and a source of bicarbonate-free or essentially bicarbonate-free concentrate(s) 573. The tap water is combined with the bicarbonate free concentrate to prepare a precursor dialysate solution which is stored in a jug or other container 570 of suitable volume. "Bicarbonate-free" refers to below measurable limits, whereas "essentially bicarbonate-free" refers to concentrations below 5 mEq/ml. The dialysate fluid circuit 510 can be primed with precursor dialysate fluid containing 0-0.5 wt %, or 0-0.05 wt %, or 0-0.01 wt % bicarbonate salt, or other values, based on total weight of precursor dialysate fluid in the fluid circuit. As indicated, the bicarbonate free or essentially-free concentrate can contain other electrolytes, such as sodium chloride, and osmotic agents such as dextrose, and/or other components that are soluble in water in conditions experienced during a dialysis treatment. The bicarbonate free or essentially free concentrate is shown as pre-mixed with the tap water in FIG. 5. Another option may be addition of the bicarbonate free or essentially free concentrate to purified tap water in tubing 530 after discharged from the sorbent cartridge 522. The precursor dialysate solution 571 can be introduced into the dialysate circuit 510 including the expandable reservoir 524, though tubing 574, by opening valve 594 (e.g., a two-way (shut-off/open) valve) to allow the flow of the precursor dialysate solution from source 570 into tubing 520 of the dialysate circuit by gravity or pump action, such as using pump 582. When tap water or other non-sterile water is used in the preparation of the precursor dialysate solution, the tap water content of the precursor dialysate solution needs to be passed through the sorbent cartridge 522 for purification to AAMI quality before it is passed through the dialyzer 512. To do this, clamps/valves 591 and 592 can be used to block fluid flow between the dialysate circuit 510 and the dialyzer 512. The valve 594 can be opened and the precursor dialysate solution can be pumped into the fluid circuit 510 and through the sorbent cartridge 522. A predetermined volume of precursor dialysate solution can be used for the priming operation. After completing the introduction of the precursor dialysate solution into the dialysate circuit 510, the valves/clamps 516 and 518 can be opened so that dialysate can flow between the dialyzer 512 and the dialysate circuit 510 concurrent with blood flow from and to the patient through the dialyzer to support a dialysis treatment. Suitable sensing, monitoring, and/or metering systems, as known to those of skill in the art, can be used for the in-situ preparation of dialysate within dialysate circuit 510, and to make appropriate adjustments to the composition of dialysate within dialysate circuit 510 during a dialysis treatment. A conductivity meter 552, for instance, can be included in the dialysate circuit 510. As an alternative to forming precursor dialysate solution using tap water pre-mixed with the concentrate (such as shown in FIG. 5), dialysate can be made in-situ, that is, within the dialysate circuit of the dialysis system such as described in regard to FIG. 6 herein. Further, a method using sterile water (ultrapure water) to prime the dialysate circuit is described herein as an option in the descriptions of FIG. 6 herein.

The dialysis system can comprise an interface, in the form of a graphical user interface, with touch screen buttons, a physical keypad, a mouse, or the like (not shown), which can be manipulated to cause the system to start operation in either a treatment mode or a priming mode. The priming mode can include the in-situ preparation of the dialysate. The dialysis system can include a manifold that comprises one or more valves and that can be controlled to provide different valving schemes and flow paths. Exemplary manifolds and system components related to the use of a manifold, which can be used, include those shown and described in U.S. Patent Application Publication No. US 2011/0315611 A1, to Fulkerson et al., published on Dec. 29, 2011, which is incorporated herein in its entirety by reference. When instructed to operate in a treatment mode, the controller generates a signal, in response to a treatment mode command, to cause a manifold valve to switch from an open, priming state to a closed, treatment state. When instructed to operate in priming mode, the controller generates a signal, in response to a priming mode command, to cause the manifold valve to switch from a closed, treatment state to an open, priming state. One of ordinary skill in the art would appreciate that the control and user command functions can be effected by incorporating one or more processors executing programming embodying the aforementioned instructions, and appropriate programs can be stored in local memory. Such a dialysis controller is described in more detail in the description of FIG. 14 herein.

Figure 6:
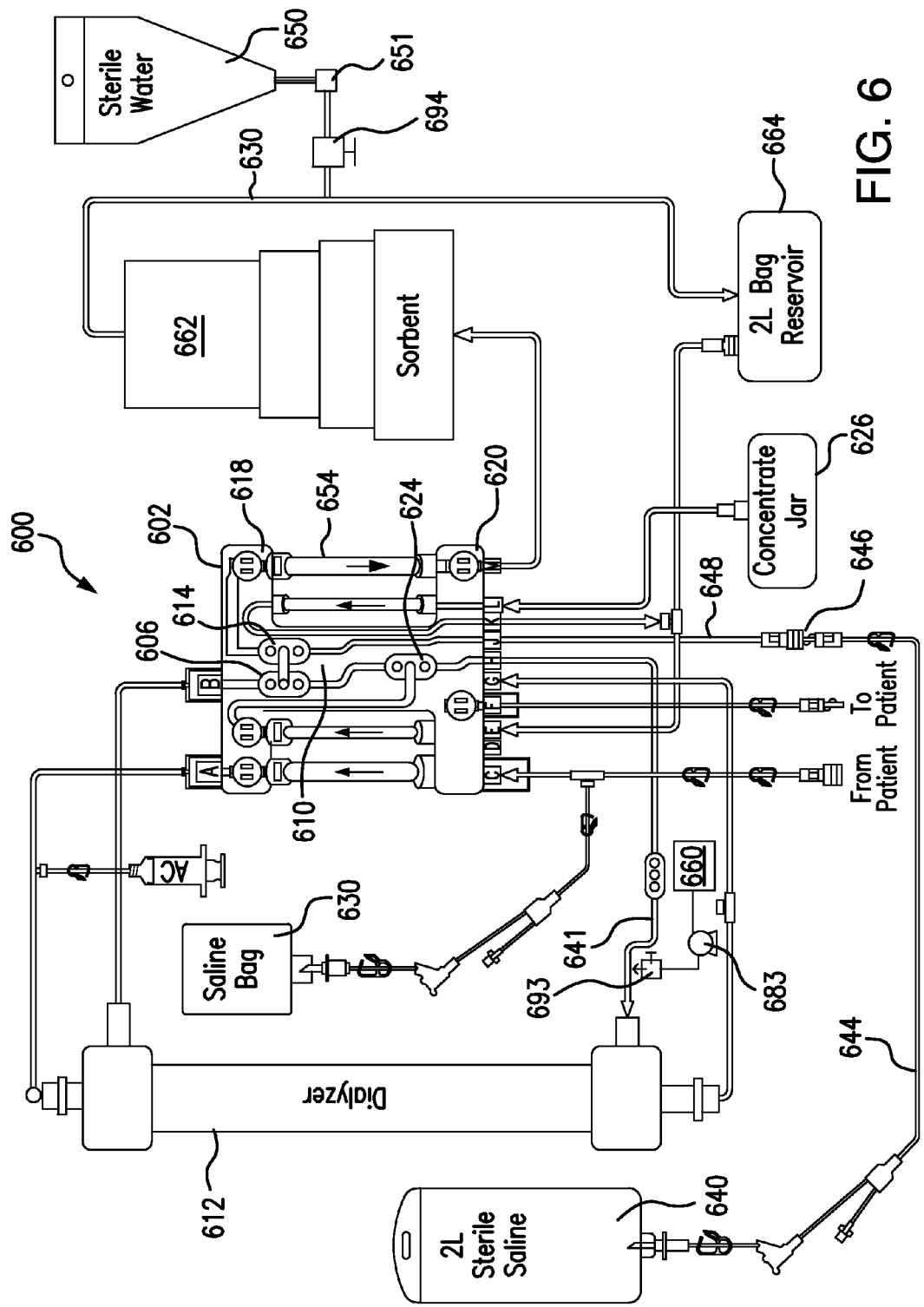
FIG. 6 is another schematic diagram of a dialysis system in accordance with an example of the present application.

With reference to FIG. 6, a dialysis system 600 is shown as configured for hemodialysis. Dialysis system 600 comprises a manifold 602 that includes four pump tube segments or headers each shown with an arrow in the middle thereof to denote the flow of blood or dialysate during a dialysis treatment. The pump tube segments are bonded to ports in manifold 602. A number of ports are provided in the manifold, which connect with tubes external to the manifold to allow the flow of various fluids in and out of the manifold. These ports are connected to various tubes in the dialysis system as follows: Port A—blood to dialyzer 612; Port B—dialyzer output (for used dialysate); Port C—blood from a patient; Port D—heparin for mixing in the blood; Port E—reservoir output (for fresh dialysate); Port F—dialyzer input (for fresh dialysate); Port G dialyzer output (blood); Port H—patient return (for clean blood); Port J—connects to prime and drain line; Port K—concentrate output to dialysate circuit; Port L—concentrate or infusate input (e.g., input of electrolytes, such as K, Ca, Mg) from concentrate jar 626; and Port M—sorbent cartridge input for used dialysate flow into sorbent cartridge. A tube segment, formed as a pathway molded into the manifold structure, can connect the fluid flow of heparin, entering via Port D, to the fluid flow of blood, entering via Port C. The operation of and more details about many of the ports shown, as well as some other aspects of the dialysis system shown, can be ascertained by reference to U.S. Patent Application Publication No. US 2011/0315611 A1, particularly to FIG. 86 thereof, which publication and figure are incorporated herein in their entireties by reference.

The ports can be designed for circuit tubing 0.268"× 0.175" tubing or anticoagulant and infusate tubing 0.161"× 0.135". The tubing ports can be bonded with a suitable solvent. It should be appreciated that the valves shown can be positioned in different locations within the manifold. In the arrangement shown, valve 606 is positioned in a central vertical portion 610 of manifold 602 adjacent to and parallel to valve 614. Also on central vertical portion 610 of manifold 602, which connects a top horizontal portion 618 and a bottom horizontal portion 620 together, is another valve 624. Valve 624 is on the bottom portion of central vertical portion 610 and positioned substantially below and centered between valves 606 and 614. A supply of saline in the form of a saline bag 630 can be used to prime the blood circuit of dialysis system 600 and/or to infuse saline into a patient, for example, to hydrate the patient and replace fluid lost during a dialysis treatment. The valves provided in the manifold 602 to control fluid movement through the manifold can be magnetic and/or solenoid valves or other kinds of valves.

The supply of sterile water 650 is fluidly connected to tubing 630 that carried regenerated dialysate discharged from the sorbent cartridge 662 to supply sterile dilution water in the later or final period of dialysis treatment to reduce sodium concentrations, as indicated. Orifice flow controller 651 and valve or clamp 694 is used in conjunction with the supply of sterile water 650 as indicated to control flow and flow rate, respectively, of the sterile dilution water into tubing 630. The source of bicarbonate solution 660 is fluidly connected to tubing 641 connected to the dialyzer inlet for dialysate. Bicarbonate solution is added to the regenerated dialysate in tubing 641 during an initial early time period of a dialysis treatment as indicated. The source of bicarbonate solution 660 can be a supply container (e.g., a flexible bag or fix-shaped container) that holds concentrated bicarbonate solution which is stored in the container as a premixed solution. The bicarbonate source 660 alternatively can be an assembly that permits the bicarbonate solution to be prepared on demand from dry powder using a container (e.g., a bag) filled at least in part with dry bicarbonate powder with inlet and outlet ports, wherein the bag has a water inlet which allows entry of purified water into which the powder dissolves and an outlet from which resulting concentrated bicarbonate solution exits the bag, which can be used as a treatment solution for regenerated dialysate in the present invention. An example of such a bicarbonate source using dry bicarbonate powder which can be adapted for use in this respect is a Bibag® system (Fresenius Medical Care North America). Pump (or orifice flow controller) 683 and valve 693 can be used to control the flow and flow rate, respectively, of the bicarbonate solution from the source 660 to tubing 641. Expandable reservoir 664 is used to store regenerated dialysate, if and when needed, and manage dialysate flow. As an example, the expandable reservoir 664 can hold two liters of dialysate and has the capacity to hold up to six liters of dialysate and effluent from the patient. Although the expandable reservoir 664 shown in FIG. 6 is schematically shown as substantially rectangular for simplification, it is to be understood that expandable reservoir 664 can be a reservoir as described herein, for example, as part of an expandable reservoir and heated reservoir holder combination.

With respect to a priming mode, a bloodline from a patient into the manifold 602 is not connected and therefore, no blood is flowing, or capable of flowing, into the manifold. Rather, dialysate passing from a source passes into the manifold through a plurality of ports and through a dialysate in-line is connected to a two-way valve port. Precursor dialysate solution can be premixed (water plus bicarbonate free or essentially-free concentrate) before introduction into the dialysate circuit or it can be made in-situ, that is, within the dialysate circuit of the dialysis system 600 shown in FIG. 6. As an alternative to forming precursor dialysate solution using tap water (such as shown in FIG. 5), ultra-pure (sterile) water can be used in the precursor dialysate solution. A low-volume supply of ultrapure (sterile) fluid, for example, a two-liter supply of sterile saline 640, can be introduced into the dialysate circuit through a supply tube 644. Although the ultrapure fluid shown in FIG. 6 is exemplified as sterile saline, it is to be understood that any ultrapure fluid can be used and the source of sterile saline can instead be a source of any other ultrapure fluid. Supply tube 644 can be connected at a connection 646 to a fill/drain tube 648 to form a fluid communication between the two tubes. An end of fill/drain tube 648 opposite connection 646 is bonded to manifold 602 at port J, as shown. If used to prime the system, after the sterile saline, or a portion of it, is drained, loaded, or otherwise transferred from sterile saline supply 640 into the dialysate circuit, sterile saline supply 640 can be disconnected from fill/drain tube 648 at connection 646 and connection 646 can be capped until the dialysate circuit is ready to be drained. Gravity can be used to assist transfer of the sterile saline from sterile saline supply 640 into the dialysate circuit, although the sterile saline can also be pulled into the dialysate circuit by using a peristaltic pump in the base instrument, which acts on pump header 654 of manifold 602. In the arrangement shown, the sterile saline from supply 640, if used to prime the system, first enters the dialysate circuit between the dialyzer (612) and the sorbent (sorbent cartridge 662). In such an arrangement, the "first tubing" to which the source of sterile saline is connected includes a tubing from dialyzer 612 to manifold 602, a pathway through manifold 602, and a tubing from manifold 602 to sorbent cartridge 662. Tap water or precursor dialysate solution with prepared with same, if used, can be introduced into the system at a similar location.

Figure 7:
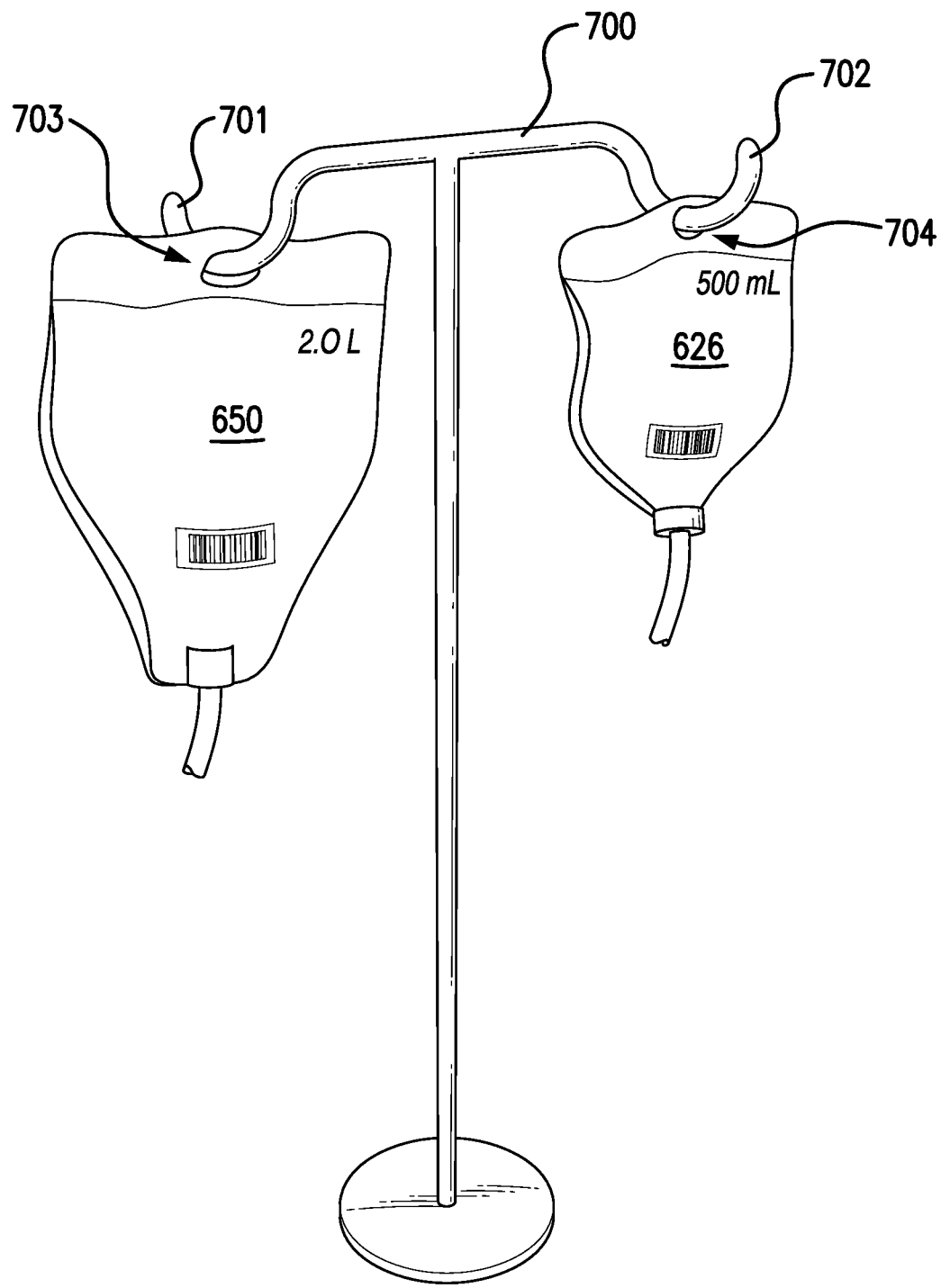
FIG. 7 is a front perspective view of a hanger assembly holding a 2.0-liter bag of sterile dilution fluid and a 0.5-liter bag of sterile electrolyte solution in accordance with an example of the present application.

FIG. 7 is a front perspective view of a hanger assembly 700 holding a 2.0-liter bag of the sterile dilution fluid 650 (and a 0.5-liter bag of sterile electrolyte solution 626 (K, Ca, Mg)) for introduction during a dialysis treatment as indicated. If used, a bag of ultrapure water can be arranged using a similar hangar assembly. The hangar assembly can include hooks 701 and 702 for holding the bags 650 and 626 by eyelets or holes 703 and 704 formed in the bags.

As indicated, the orifice flow controller, such as device 651 in FIG. 6, is used in combination with the sterile dilution water supply bag 650 and the flow line of the regenerated dialysate discharged from the sorbent cartridge to provide constant predetermined flow rates of the dilution water into the flow line of the indicated regenerated dialysate solution. As also indicated, instead of using a pump for component 683, an orifice flow controller can be used for that component to control the flow and flow rate, respectively, of the bicarbonate solution from the bicarbonate source 660 to tubing 641. If an orifice flow controller is used instead of a pump for component 683, a gravity feed configuration for a supply bag or other container of bicarbonate solution that is similar or substantially similar to that described herein for the sterile dilution fluid supply 650 can be used to assist transfer of the bicarbonate solution from such a bicarbonate supply bag or other container through the orifice flow controller 683 into the dialysate circuit. The bicarbonate solution can also be pulled into the dialysate circuit by using the peristaltic pump in the base instrument or advanced into the dialysate circuit by positive flow pressure in bicarbonate solution obtained from an in-bag preparation technique using dry powdered bicarbonate and inlet/outlet fluid flow as indicated.

Figure 8:
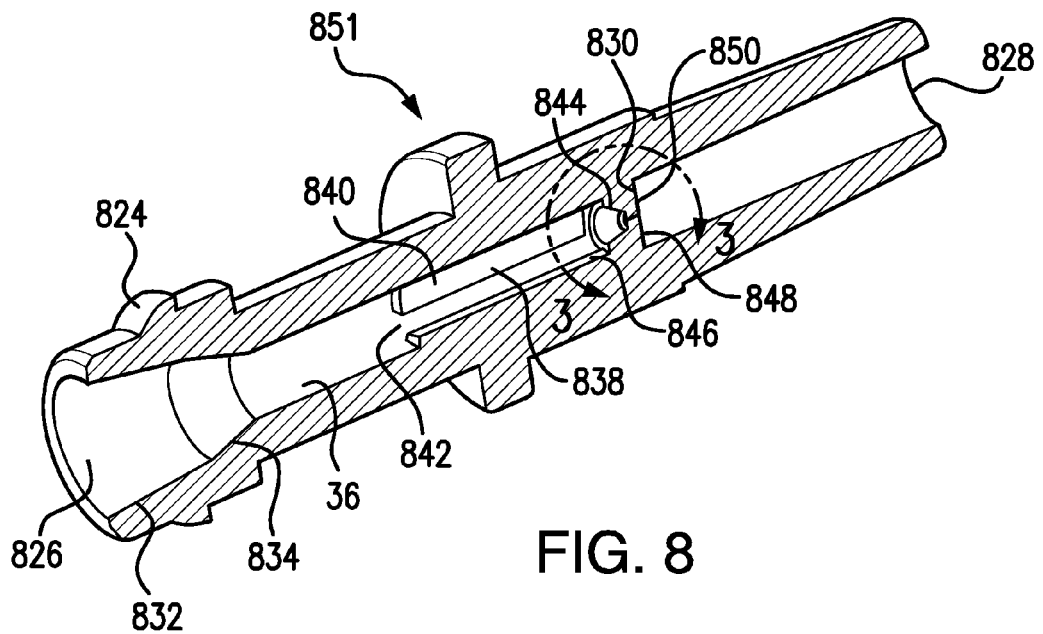
FIG. 8 is a cross-sectional perspective view of the orifice flow controller formed within a body for use with a sterile dilution supply system in accordance with an example of the present application.
Figure 9:
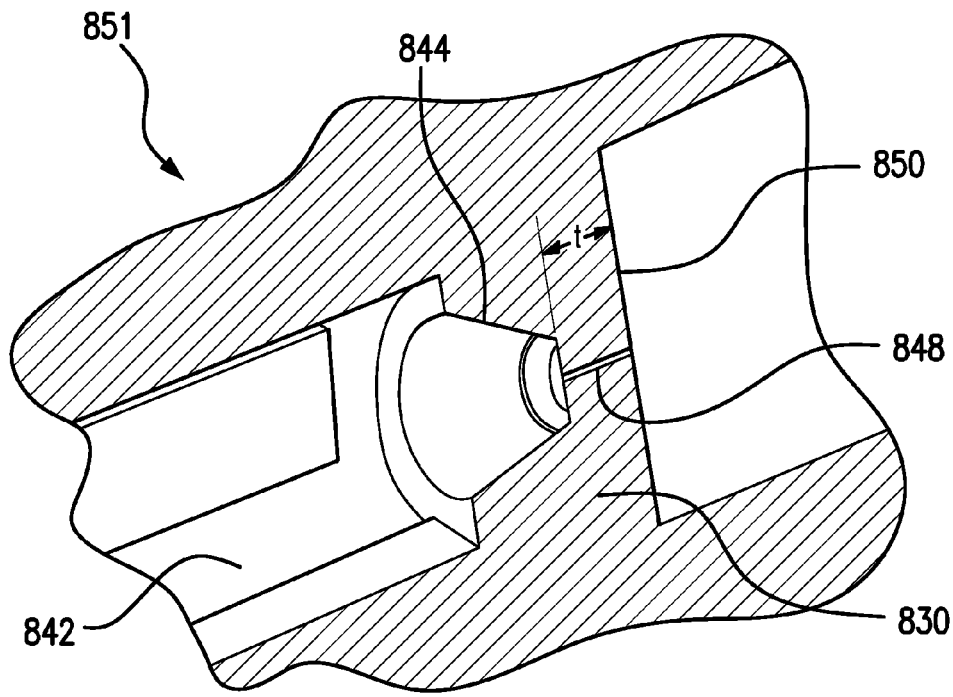
FIG. 9 is an enlarged partial cross-sectional perspective view of the orifice flow controller for use with a sterile dilution supply system in accordance with an example of the present application restrictor.

When a liquid flows through a constriction, such as an orifice or capillary of reduced diameter in a wall separating two sections of tubing, a pressure differential can be created between the tubes which can control the rate of flow within the tubing system. An orifice flow controller such as used in intravenous administration sets can be adapted for use in the present invention for this purpose for an orifice flow controller which can be used in the indicated controlled feeding of the sterile dilution fluid, the controlled feeding of the bicarbonate solution, or in both. Capillary orifice flow controllers (restrictors) or orifice flow controllers, such as shown in U.S. Pat. No. 5,409,477, which is incorporated in its entirety by reference herein, can be adapted for use in this regard. FIGS. 8 and 9, for example, show enlarged cross-sectional views of an orifice flow controller 851, which can represent the orifice flow controller 851 as shown in FIG. 6. The flow rate can be determined by the size of an orifice formed within the body of the orifice flow controller. Referring to FIGS. 8 and 9, an orifice flow controller 851 is shown that includes an elongated body 824, with an inlet port 826, and an outlet port 828 formed therein. Separating the inlet and outlet ports 826, 828 is a barrier-like wall or orifice plate 830. Inlet port 826 has first and second inward distal tapers 832, 834 to a substantially constant diameter medial section 836. The distal portion 838 of medial section 836 has a plurality of raised longitudinal ribs 840 (four in illustration) along the interior wall 842 extending to orifice plate 830. Proximal surface 846 of plate 830 can be formed with a tapered nipple shaped depression 844 therein, as best seen in FIG. 8. An orifice 848 can be formed through plate 830, which defines a flow control passage, and which extends from about the center of depression 844 to outlet port 828. The orifice 848 has a predetermined cross-sectional flow area which provides accurate predetermined flow communication between inlet port 826 and outlet port 828. Orifice 848 can be produced by drilling through plate 830 with a laser or other narrow frequency light emitting cutting device. The diameter of orifice 848 can range from about 0.0011 to about 0.0050 inches dependent upon the rate of administration of solution as required for the particular patient. The orifice flow controller 851 described and shown in the associated figures, the body 824 was formed from a polycarbonate material. The orifice 848 can be drilled to a diameter of 0.0029 inches, through orifice plate 830, which has a thickness, t, of 0.012 inches with a tolerance of +0.002 inches. The orifice 848 can be drilled using an excimer laser or other laser. The ratio of the thickness of plate 830, between the base of depression 844 and the distal surface 850 of plate 830, to the diameter of orifice 848, can be limited to a maximum of 10:1. Conversely, orifice 848 can be at least one tenth of the length, L, of the flow control passage through plate 830 at a point adjacent to the orifice 848. In the orifice flow controller 851 as illustrated, the ratio of thickness, t, to the diameter of orifice 848 can be about 5.2:1. Outlet port 828 extends from the distal surface 850 of orifice plate 830 to the outlet 852. Outlet port 828 has a substantially constant circular cross-section along its length as best seen in FIG. 8. Other optional features of the orifice flow controller are described, for example, in the incorporated U.S. Pat. No. 5,409,477. The orifice flow controller can be formed in polymer, metal, ceramic, composite, or other material that can be shaped and/or machined to provide the requisite structure to properly function as intended. The material used for the orifice flow controller can be a medical-grade plastic (e.g., polyethylene, polysilicone, or others), or other materials.

The expandable reservoir, such as represented as reservoir 524 in FIG. 5 and reservoir 664 in FIG. 6, can be provided with one or more features that minimizes the volume of dialysate needed for efficient operation of the dialysate circuit. The expandable reservoir can comprise a reservoir inlet and a reservoir outlet, and the reservoir outlet can be positioned at a bottom of the expandable reservoir. One or more slanted bottom walls can be included at the bottom of the expandable reservoir such that any dialysate in the very bottom of the expandable reservoir is directed toward the reservoir outlet. A funnel-shaped bottom wall, trough-shaped bottom wall, inverted hollow pyramid-shaped bottom wall can be used, a U-shaped bottom wall can be used, a V-shaped bottom wall can be used, or any other of a variety of shapes can be used that channel dialysate in the expandable reservoir toward the reservoir outlet. The reservoir can be constructed as a flexible bag and a reservoir holder can be provided that defines the shape of the bottom wall of the expandable reservoir. If a reservoir holder is used, it can comprise one or more heating elements and one or more temperature sensors that can be powered and monitored to maintain an appropriate temperature of dialysate in the expandable reservoir and in the dialysate circuit.

The sterile dilution water bag can be provided with one or more similar features as indicated for the expandable reservoir that minimizes the volume of dialysate needed for efficient operation of the dialysate circuit.

Figure 10:
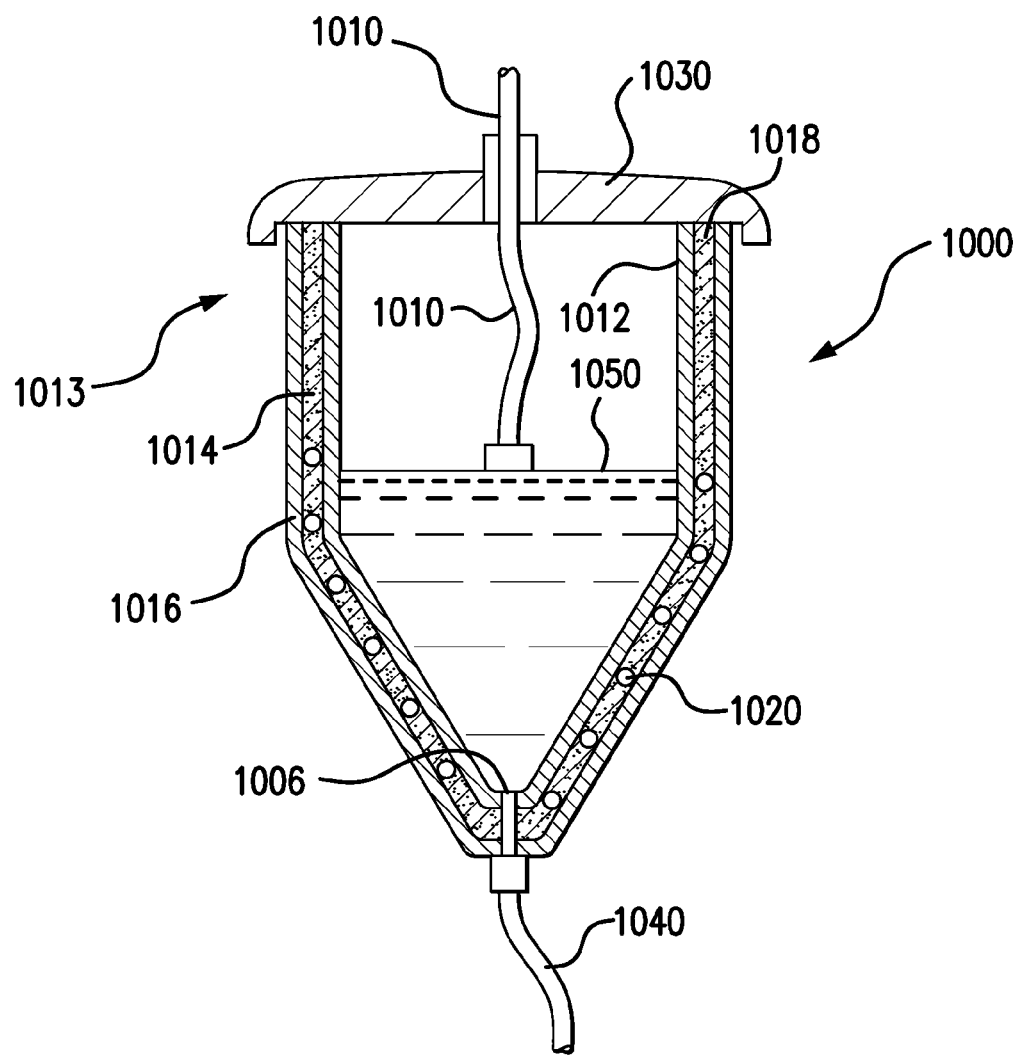
FIG. 10 a front, cross-sectional view of an expandable reservoir in a reservoir vessel in accordance with an example of the present application.

FIG. 10 is a front, cross-sectional view of an expandable reservoir 1000 in a reservoir vessel 1013, which can be used for the expandable reservoirs 524 and 664 in FIGS. 5 and 6. As shown in FIG. 10, tubing 1010, which can correspond to tubing 530 and 630 in FIGS. 5 and 6, can be pre-threaded through a disposable lid 1030, or, disposable lid 1030 can be provided with a slot and/or with connectors for accommodating or connecting to tubing 1010 and for providing a passage for tubing 1010 to enter reservoir vessel 1013. Tubing 1040, which can represent tubing 540 in FIG. 5, can be bonded or otherwise connected a reservoir outlet 1006 at the bottom of expandable reservoir 1000. Regenerated dialysate 1050 is held in the reservoir vessel 1013 until discharged through outlet 1006 into tubing 1040. Reservoir vessel 1013 can include an inner wall 1012, a heating element layer 1014, and an outer wall 1016. Heating element layer 1014 does not necessarily require one or more sidewalls but instead can be defined by and situated between inner wall 1012 and outer wall 1016. Heating element layer 1014 can comprise a heat-conductive foam 1018 or other heat-conductive material, and one or more heating elements 1020. Heating element 1020 shown in FIG. 10 is in the form of a single continuous coil.

In further regard to the configuration and operation of the dialysis system, a single two-way valve can be incorporated into the physical body of the indicated manifold (602, FIG. 6) and manipulated to switch between a treatment mode of operation and a priming mode of operation. The manifold can comprise a two-way valve which, if activated or switched from a first positioned (e.g. closed) to a second position (e.g. open), causes a change to the internal flow path of liquid within the manifold. As a result of this flow path change, the blood and dialysate circuits, which, when the valve is closed, are fluidly isolated from each other, are now placed in fluid communication with each other. Preferably, no additional valves or switches need to be manipulated in order to achieve this state change, namely, to cause separate blood and dialysate circuits to become fluidly connected. Further details of such manifolds, valves, priming modes, and treatment modes, that can be used and carried out by the system and methods of the present invention, are taught in U.S. Patent Application Publication No. US 2011/0315611 A1. The valve switch may be effectuated by any means known in the art, including by physically manipulating a mechanical control on the surface of the manifold or electronically through the operation of a dialysis machine causing a change to the valve state through an interface between the dialysis machine, which has a controller to control the state of the valve in accordance with a user selected operational mode, and a valve interface integrated into the surface of the manifold. A filter, such as a 0.22 micrometer filter, can be used to help remove any undesirable substances in the dialysate circuit if the sorbent cartridge is inadequate at producing essentially sterile dialysate. The filter can be positioned in-line with the reservoir input line, proximate to Port E of the manifold, as shown in FIG. 6, and can be used both during priming and during treatment.

The indicated valves that can be used in the dialysis system can be two-way valves and operate by having valve actuators, which are mounted on a base instrument (not shown) of the dialysis system, compress an elastomeric diaphragm over a volcano seal to prevent dialysate flow through its respective pathway. The manifold can contain structures that allow for fluid pressure monitoring across diaphragms through the use of sensors in the base instrument. Fluid is allowed to flow from channels on a front cover side of the mid-body through inlet and outlet holes underneath the diaphragm on a back cover side. The cross-sectional pathway through the interior of the pressure sensing structure is at least equivalent to 0.190". The valves and diaphragms can be made from a variety of different materials and by different processes. The elastomeric components can be made from silicone or made from a variety of thermoplastic elastomers. Two shot molding can be used to attach the valves and diaphragms to the back cover. Two shot molding of valves and diaphragms can be used such that there is no need to individually assemble these parts into the manifold, thus reducing labor costs and improving the quality of the manifold assembly.

Pumping components in the manifold design can comprise polyvinyl chloride (PVC) pump segments or pump headers. Such pump headers, when combined with a rotary peristaltic pumping system of the base instrument, can provide the flow of blood, dialysate, concentrated electrolytes, and concentrate or infusate, useful for the in-situ preparation of dialysate and for maintaining the composition of the dialysate during a dialysis treatment.

Plastic tubing, conventional medical tubing, and the like, can be used for the various indicated tubings. The circuit tubing for dialysate, concentrate, infusate, bicarbonate solution, sterile water, and anticoagulant can be made of thermoplastic material, such as polyvinyl chloride, polycarbonate, or other polymeric materials that are sufficiently structurally robust, sanitary, and inert to the fluids passed through them in a dialysis treatment. Preferably, the tubing is made of disposable material. The circuit tubing material for dialysate, concentrate, infusate, and anticoagulant is preferably kink resistant, such as the tubing referred to as COLORITE, OR UNICHEM PTN 780 (80 A durometer) extruded by Natvar, available from TEKNIplex, of King of Prussia, Pa. The tubing dimensions for the dialysate lines can range from about 0.268"×0.189" to about 0.268"×0.175". Tubing can be provided to connect together, in fluid communication, the various components of the dialysate circuit. Each of the tubings can independently comprise a continuous length of tubing, two or more separate tubings that are connected together, or the like.

Various connectors, valves, diverters, junctions, taps, septa, and inlets can be provided along, and/or as part of, each of the tubings. For example, along the tubing, between the dialyzer outlet and the sorbent cartridge inlet, a Y connector can be provided so that a fluid line can be connected to the first tubing. The fluid line can supply precursor dialysate solution into the first tubing. To prime the dialysate circuit, precursor dialysate comprising tap water or a source of ultrapure fluid (for example, from a collapsible bag of ultrapure fluid), can be hooked up to the Y connector, for example, by removing a cap protecting an opening, a branch, or an inlet of the Y connector. Once a source of precursor dialysate solution is connected to the first tubing, a pump, gravity, or a combination thereof, can be used to force the precursor dialysate solution into the dialysate circuit. One or more dialysate circulating pumps, such as a peristaltic pump, can be provided along the dialysate circuit, to move dialysate, or precursor dialysate solution, in the dialysate circuit. The dialysate or precursor dialysate solution can be moved in a direction from the first tubing toward the sorbent cartridge inlet, from the sorbent cartridge outlet toward the reservoir inlet, from the reservoir outlet to the dialysate inlet, and from the dialysate outlet back toward the sorbent cartridge inlet. The Y connector can comprise a one-way valve, flap valve, or the like, to prevent ultrapure fluid or dialysate from moving through the Y connector and upwardly toward the container or bag that originally held the ultrapure fluid. After precursor dialysate solution is loaded into the dialysate circuit, the opening to the Y connector through which the fluid entered, can be closed off, for example, by disconnecting the source of precursor dialysate fluid and capping the opening to the Y connector. The circulating pump can be turned off or paused during the disconnection and capping. The bicarbonate free or essentially free concentrate used for prime and/or electrolytes infused during a dialysis treatment (e.g., K, Ca, Mg), can be provided to the dialysate circuit, directly, such that they are mixed with the dialysate fluid in-situ, that is, within the dialysate circuit. A liquid supply of electrolytes, such as an electrolyte solution, can be used. The electrolytes can be provided from a sterile container or can be pre-mixed and dispensed to a dispensing container. The electrolytes can be provided in the form of a sterile aqueous solution, for example, packaged in a collapsible bag. The bag can be connected, as by a tube, to a Y connector in the third tubing, between the reservoir outlet and the dialysate inlet. The same kind, or a similar Y connector as can be used for connecting a source of ultrapure fluid, if used, to the first tubing, and can be used to connect the source of electrolytes to the third tubing.

The electrolytes (e.g., K, Ca, Mg) can be introduced to the dialysate circuit at any location along the dialysate circuit. Introducing the electrolytes at a junction that is downstream of the sorbent cartridge, and upstream of the dialyzer, can prevent electrolytes from passing through the sorbent cartridge before they are used to treat blood in the dialyzer. One or more pumps, gravity, or a combination thereof, can be used to move electrolytes from the source of electrolytes into the dialyzer circuit. In embodiments where the electrolytes are provided as a sterile solution in a collapsible bag, a hanger assembly can be used to hang the bag. In embodiments where ultrapure fluid is used and provided in a collapsible bag, as indicated, a hanger assembly can be used to hang the source of ultrapure fluid and the source of sterile electrolytes, adjacent to and proximal to one another. Patient identification information, concentration information, packaging dates, expiration dates, other identifying indicia, a barcode, a two-dimensional barcode, a radio frequency identification tag, or the like, can be provided on the source of bicarbonate solution, the source of sterile dilution water, the source of ultrapure fluid if used for prime, on the source of bicarbonate-free or essentially free concentrate, on the source of electrolytes, or any combination of these, whether or not each source is in the form of a collapsible bag.

The dialysate can be formed in-situ from consumables that can be easily packaged and shipped together and that can be handled, manipulated, and set up at home, even by frail patients. The sorbent cartridge, expandable reservoir, and dialyzer can be packaged together for shipment, for example, in a hermetically sealed bag. The components can be sterilized, for example, by radiation, before, during, or after being packaged. The sorbent cartridge, expandable reservoir, and dialyzer can be empty, that is, free of liquids, when they are packaged and shipped. The source of ultrapure fluid can be packaged separately from the sorbent cartridge, expandable reservoir, and dialyzer and can be shipped separately from, or together with, these disposables. The source of sterile dilution water can comprise a container, such as a collapsible plastic bag, having a holding volume of about 3 liters or less, for example, 2.5 liters or less, 2 liters or less, 1.5 liters or less, 2.5 liters, 2 liters, 1.5 liters, or the like. The source of ultrapure water, if included, can comprise a container, such as a collapsible plastic bag, having a holding volume of about 3 liters or less, for example, 2.5 liters or less, 2 liters or less, 1.5 liters or less, 2.5 liters, 2 liters, 1.5 liters, or the like. If premixed with sterile water, the source of bicarbonate solution can comprise a container, such as a collapsible plastic bag, having a holding volume of about 1 liters or less, for example, 750 mL or less, 500 mL or less, 250 mL or less, 100 mL or less, 50 mL or less, or other volumes, depending in part on the concentration of the bicarbonate. These indicated volumes can apply to saturated bicarbonate solutions. If premixed on-site where dialysis treatment is to be provided, bicarbonate can be supplied in dry particulate form in container or packet for combination on site with sterile water that is jointly or separately supplied. The solid components of the bicarbonate free or essentially free concentrate, such as sodium chloride and dextrose, can be supplied in particulate form premixed in the same container or packet or in separate container or packets. The source of electrolytes can be packaged and shipped together with, or separately from, the source of bicarbonate, source of sterile dilution water, bicarbonate free or essentially-free concentrate, and ultrapure fluid (if used). The source of electrolytes can comprise a jar containing an aqueous solution of electrolytes. The electrolytes can be provided in a powdered form, such as in a packet that can be dissolved in water to form an electrolyte solution. The electrolyte solution can be pre-mixed, or mixed, and then poured into an electrolyte container or jar. The dialysate circuit can include a fluid communication, such as a tubing, that provides a conduit for moving electrolytes from the electrolytes container, jar, or bag, into the dialysate circuit. The system or the disposables can further comprise an empty jar for containing electrolytes and the electrolytes can be prepared and supplied to the jar after the dialysate circuit is otherwise set-up. If the source of electrolytes comprises a collapsible bag, the collapsible bag can have a holding volume of about one liter or less, for example, about 0.5 liter or less, 300 ml or less, 200 ml or less, 100 ml or less, 200 ml, 100 ml, 50 ml, or other volumes.

Figure 11:
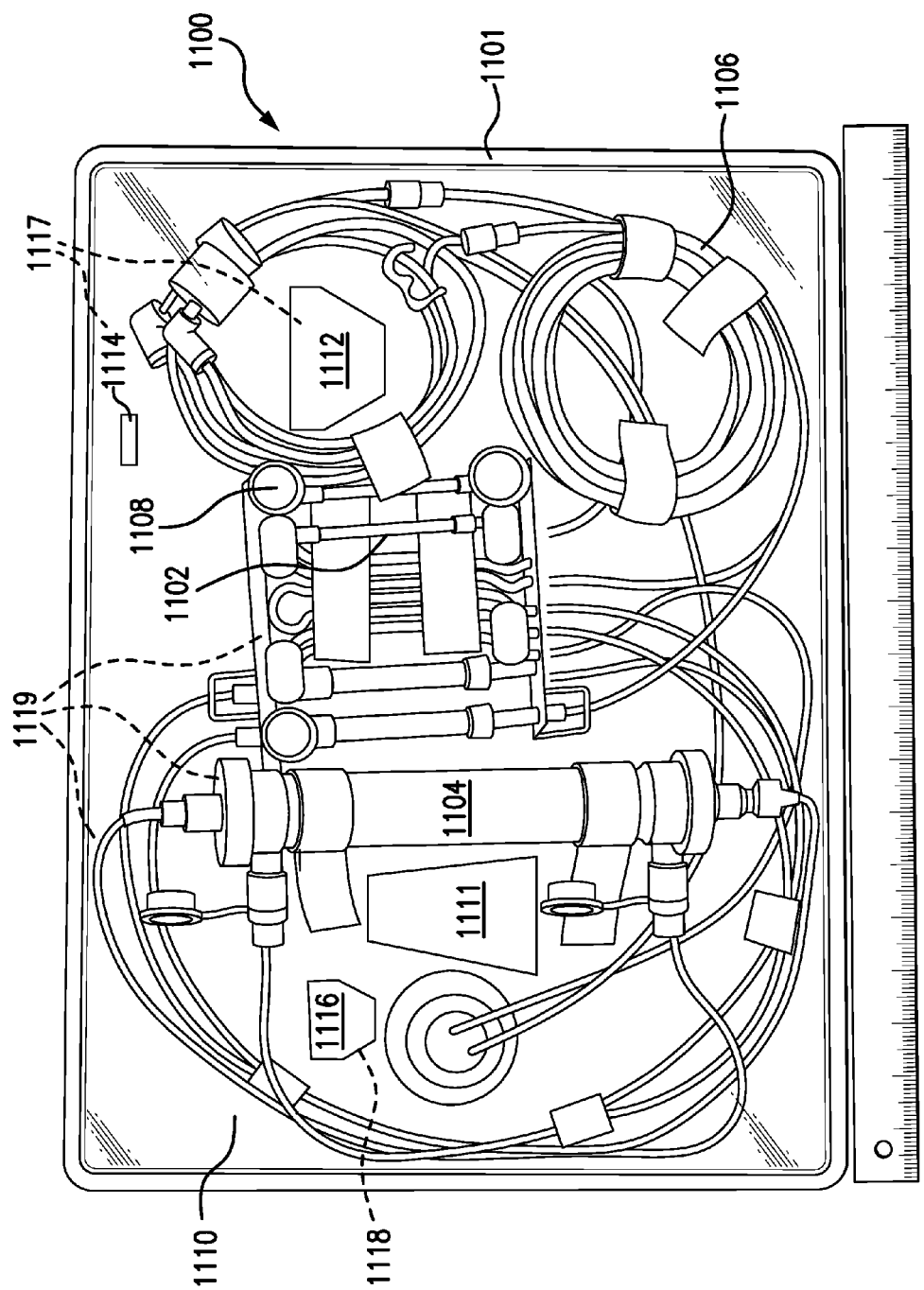
FIG. 11 is a top view of an exemplary disposables kit that can be used in accordance with the present invention in accordance with an example of the present application.

A dialysis system disclosed herein can be designed to use a plurality of disposable components. Referring to FIG. 11, a kit 1100 that includes disposables for use in the system are shipped in packaging, preassembled on a tray 1101. Tray 1101 can be placed on top of the dialysis system controller unit workspace, thereby permitting easy access to, and management of, the required disposables, which can be of particular importance for home users. The controller unit can be waterproof rated, so that, in case of a liquid spill, the liquid should not seep into and damage the controller unit. The kit 1100 can contain a manifold 1102, a dialyzer 1104, and tubing 1106 which are all preattached. Valves 1108 can be provided as part of the manifold. An ammonia sensor or other sensors can be included (not shown). The kit also can include a sorbent cartridge 1111. A supply container (e.g., flexible bag) 1112 containing from about 1.5 liters to about 2.0 liters of sterile water, can be included as well as an orifice flow controller 1114. A supply container 1116 that is a source of bicarbonate solution can be included. Supply container 1116 can be a container that contains concentrated bicarbonate solution, or a container containing dry bicarbonate powder wherein the container has a water inlet which allows entry of purified water and an outlet from which concentrated bicarbonate solution exits the container. A reservoir bag 1110 also can be included, and all the disposables can be preattached and configured for direct installation into the dialysis system, by a user. More specifically, the disposable components, particularly the fully disposable blood and dialysate circuits, are prepackaged in a kit (which includes dialyzer, manifold, tubing, reservoir bag, bag of sterile water (e.g., 2 L), orifice flow controller, bag of bicarbonate solution, valves, and other components) and then installed by a user by opening a front door of the dialysis system, installing the dialyzer and installing the manifold in a manner that ensures alignment against non-disposable components such as pressure sensors, and other components. A plurality of pump shoes integrated into the internal surface of the front door can be provided to make loading of disposable components easy. The manifold only needs to be inserted and no pump tubing needs to be threaded between pump rollers and shoes. The sterile water supply container 1112 and orifice flow controller 1114 and their associated tubings can be enclosed in a common (sub)package 1117. The bicarbonate source container 1116 and its associated tubings can be packaged in a common (sub)package 1118. A pump, e.g., a syringe pump, to be used with the bicarbonate supply can form part of the existing dialysis machine or may be separately packaged with bicarbonate supply container and its associated tubings (not shown). An orifice flow controller, which may be used with the bicarbonate source container, may be packaged with the bicarbonate source container and its associated tubings (not shown). One or more of the remaining components can be placed in a common (sub)package 1119. These different packages can be supplied in a common box or other package. The various components of the kit also may be sub-packaged in different combinations thereof. This packaged, simple approach enables easy disposables loading and cleaning of the system. It also ensures that the flow circuitry is properly configured and ready for use.

Optionally, the disposable components, and particularly the manifold, can comprise an electronic-based lockout ("e-lockout") system, for example, as described in US 2011/0315611 A1. Identification data can be stored on each of the disposable components via barcode, RFID tags, EEPROM, microchip or any other identification means that uniquely identifies the disposable components to be used in the dialysis system. A reader such as a barcode reader, RFID reader, microchip reader, or any other reader that corresponds to the identification technology employed can be used, as is known to persons of ordinary skill in the art. The reader can be connected with a transceiver for wirelessly connecting to a remote database through a network such as the Internet or any other public or private network known to persons of ordinary skill in the art. The reader can be directly aligned with the identification data.

The dialyzer can be any of a variety of conventionally available dialyzers, for example, a single-use, high-flux or low flux dialyzer. Dialyzers comprising polysulfone membranes can be used. Dialyzers having membrane surface areas of from about 1.5 to about 2.5 square meters ($m^2$) can be used, for example, from about 1.75 $m^2$ to about 2.25 $m^2$. Despite using lower volume of dialysate, the dialysis system of the present invention can provide efficient dialysis treatment. High-flux dialyzers can be used, for example, that exhibit a KoA for urea of from about 1050 ml/min to about 1700 ml/min, or from about 1200 ml/min to about 1400 ml/min. Exemplary dialyzers that can be used include the OPTIFLUX® DIALYZER line of dialyzers available from Fresenius Medical Care of Waltham, Mass. F-series dialyzers from Fresenius Medical Care can also be used.

Figure 2:
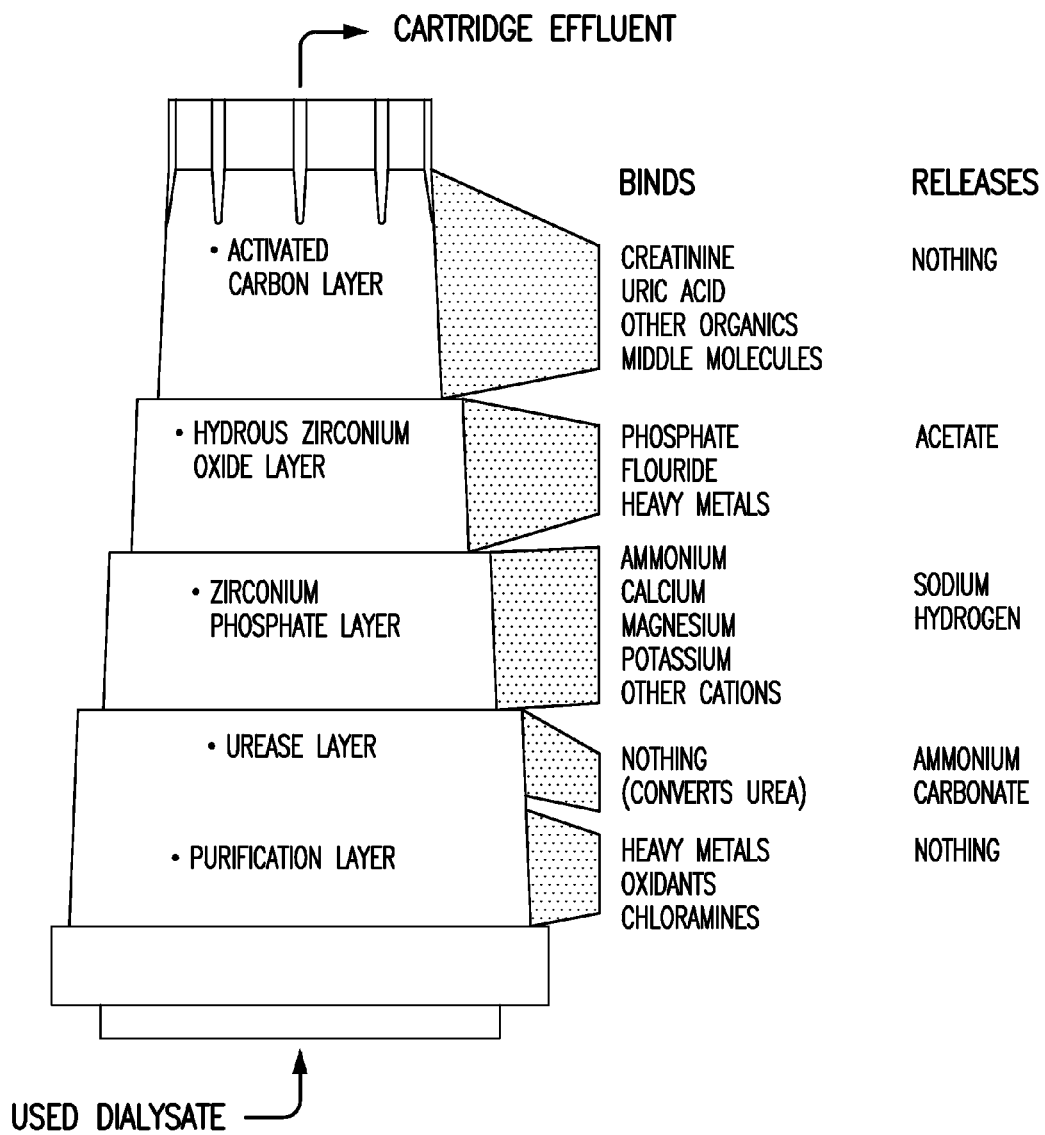
FIG. 2 is a diagram showing a cartridge and the various functions of each layer in a REDY® cartridge.

As indicated, the dialyzer comprises a blood flow path and a dialysate flow path, on opposite sides of a semi-permeable separation membrane, for example, a polysulfone membrane. A dialysate inlet and a dialysate outlet are each in fluid communication with the dialysate flow path. Dialysate can be made to flow through the dialysate flow path. The dialysate flow path can flow through the dialyzer and can be part of the larger dialysate circuit. The sorbent cartridge can be configured for regenerating used dialysate, and purifying tap water or other non-sterile water if used in a priming solution or other fluids in the dialysate circuit. The sorbent cartridge can comprise a sorbent cartridge inlet and a sorbent cartridge outlet, and can comprise a plurality of layers of different sorbent materials. Any of a variety of conventionally available sorbent cartridges can be used; however, sorbent cartridges with smaller internal volumes can require less dialysate for priming and can thus be more advantageous for the low-volume systems of the present teachings. A sorbent cartridge preferably comprises at least one urease-containing layer, at least one zirconium phosphate-containing layer, and at least one zirconium oxide-containing layer, or has a sorbent column design which can provide similar discharge profiles with respect to bicarbonate and sodium under similar conditions. Exemplary sorbent cartridges that can be used can include those shown in FIGS. 1 and 2, the SORB+ cartridge, the HISORB+ cartridge, the SORB HD cartridge, the HISORB HD cartridge, and the Advanced Sorbent Cartridge (ASC), all available from SORB™ Technology, Inc. of Oklahoma City, Okla. As indicated, the sorbent column does not need to include a bicarbonate layer, i.e., it can be bicarbonate layer free, for use in a method of the present invention. The sorbent cartridge can contain from 0 to 1 wt %, or from 0 to 0.5 wt %, or from 0 to 0.25 wt %, or from 0 to 0.1 wt % dry bicarbonate salt, or other amounts, based on total weight of preloaded materials in the sorbent cartridge.

The indicated infusion of bicarbonate solution into the regenerated dialysate can meet all bicarbonate needs for the initial time period needed during a dialysis treatment without needing to include and factor for a bicarbonate layer included in the sorbent column that continues to feed bicarbonate into the dialysate throughout a treatment session.

Figure 12:
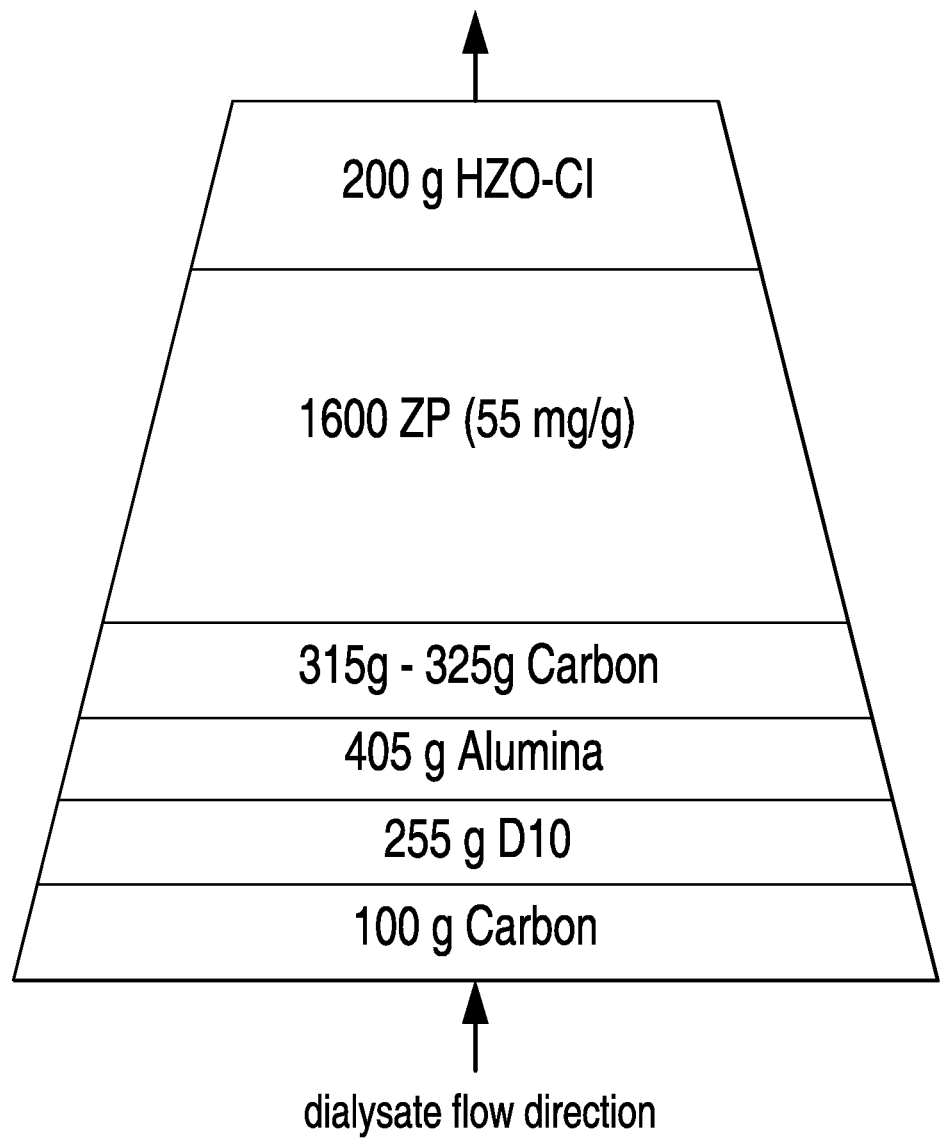
FIG. 12 is an exploded view of materials in a sorbent cartridge according to an example of the present application.

A sorbent cartridge can have layers of carbon positioned both before and after a layer comprising a urease source, in advance of a layer of zirconium phosphate and a hydrous zirconium oxide layer within the sorbent cartridge. Referring to FIG. 12, for example, the sorbent cartridge can comprise a first carbon-containing layer(s), an enzyme-containing layer(s) comprising a urease source, what follows the first carbon-containing layer within the sorbent cartridge, an optional alumina layer(s), a second carbon-containing layer(s) that follows the enzyme-containing layer and alumina layer within the sorbent cartridge, a zirconium phosphate-containing layer(s), and a hydrous zirconium oxide layer(s) that follows the zirconium phosphate-containing layer comprising hydrous zirconium oxide. In the example of the sorbent cartridge of FIG. 12, the hydrous zirconium oxide-chloride which has an alkaline pH can be used in an amount of from about 50 g to about 300 g, or from about 75 g to about 200 g, or about 100 g, or other amounts. The zirconium phosphate layer can be used in an amount of from about 650 g to about 1800 g, or from about 800 g to about 1600 g, or from about 900 g to about 1300 g, or other amounts. The carbon layer or pad can be used in an amount of from about 50 g to about 500 g carbon or other amounts, the alumina or other like material can be used in an amount of from about 100 g to about 500 g or other amounts, the blend can be used in amounts of from about 100 g to about 400 g, including from about 5 grams to about 50 grams or other amounts, and the bottom carbon layer or pad can be used in an amount of from about 50 g to about 500 g carbon or other amounts. Any effective amounts of the above-described materials can be present in the cartridge. These amounts (or any amounts recited herein) can be with respect to a cartridge having the following dimensions: 2 inches-3 inches diameter by 5 inches to 10 inches length, or having the following dimensions: 4 inches-6 inches diameter by 6 inches-12 inches length. However, it is to be understood that these amounts provide weight ratios for each layer with respect to each other layer so as to permit adjustments in any sized cartridge. The carbon can be activated carbon particles that are compacted into an activated carbon filter pad. The carbon can be activated carbon particles formed into layer of the particles that can be maintained in position by adjacent layers that adjoin the opposite sides of the carbon layer within the sorbent cartridge. Filter papers, diffusor pads, and separator rings (pads) which may be used, which can have conventional designs and structures for those types of sorbent cartridge components, such as those described in U.S. Patent Application Publication Nos. 2002/0112609 and 2012/0234762, which are incorporated in their entireties by reference herein. The various layers included in the sorbent cartridge usually are permeable to dialysate so that dialysate can continuously flow through the succession of different layers within the cartridge between the inlet and outlet thereof. Any effective amounts of the above-described materials can be present in the cartridges of the present invention. For instance, with respect to the total weight of the urease source, the urease source can be used in an amount of from about 100 grams to about 400 grams, or from about 150 grams to about 300 grams, or from about 200 grams to about 250 grams, or other amounts. Generally, the urease source, can be present in an amount of from about 22,000 IU or less to about 55,000 IU or more, or from about 28,000 IU to about 42,000 IU. The particle size of the urease source can be any effective size such as about 40 mesh or less (or less than about 0.4 mm). The remainder of the immobilized urease source can be alumina only or combinations of alumina and additional materials. Alumina is commercially available, such as from sources like Alcoa. Alumina can have the formula $Al_2O_3$. A particle size for alumina can be from about 20 microns to about 120 microns, or from about 20 microns to about 40 microns. The carbon in the carbon layers can be activated carbon in any amount and can be present in each carbon layer, for example, in an amount of from about 50 grams to about 500 grams, or from about 100 grams to about 400 grams, or from about 150 grams to about 300 grams, or from about 200 grams to about 250 grams, or from about 225 grams to about 275 grams, or other amounts. As indicated, the carbon can be activated carbon, such as activated granular carbon. The activated carbon is commercially available, such as from sources like Calgon. The activated carbon can have a particle size, for example, of from 0.4 to about 1.2 mm (or 12-50 mesh sieve), or other values. An alumina backup layer optionally can be present in an amount of from about 100 grams to about 500 grams, or from about 200 grams to about 400 grams, or from about 225 grams to about 300 grams, or other values. The particle size for the alumina in a backup layer can be the same as those indicated above for the immobilized urease source layer. The hydrous zirconium oxide (HZO) component for the cartridges can have the formula $Zr(OH)_4 \cdot nH_2O$. As indicated, the cartridge design of the present invention can permit this material to be used in acetate-free form or essentially-acetate-free form. Acetate-free hydrous zirconium oxide (HZO) can be prepared, for example, by following the methods such as disclosed in U.S. Patent Application Publication Nos. US 2010/0078387 A1 and US 2006/0140840 A1, which are incorporated in their entirety by reference herein.

The zirconium phosphate of the present invention can have an adsorption capacity for ammonia, $Ca^{2+}$, $Mg^{2+}$, $K^+$, and other cations. Further details of the zirconium phosphate and methods of making it, for example, are described in the indicated U.S. Pat. No. 6,627,164 B2, which is incorporated in its entirety by reference herein. The zirconium phosphate can be used in any amount, subject to practical constraints of the size of the cartridge into which it may be loaded or positioned. As an option, the amount of the zirconium phosphate is a sufficient amount to remove at least partially if not substantially or entirely all of the ammonia present in the spent fluids while providing this performance with reduced sodium loading, such as compared to the indicated previous cartridge designs. Other materials that can also be present in the sorbent cartridge include, but are not limited to, activated alumina, zeolites, diatomaceous earth, and other conventional adsorbent(s), fillers, glass beads, and the like. A single cartridge can be used which combines all of the above-described materials. In another example, a series of cartridges can be used wherein the combination of the above-described materials can be present in different cartridges that are fluidly coupled together and/or with different layers of the combination placed in separate cartridges.

The sorbent systems of the present invention, as indicated above, can be used in a variety of dialysis systems for regeneration or purification of dialysates (e.g., HD) or PD solutions. In a less complicated design, spent or used dialysate or PD solutions can simply be passed through one or more cartridges to purify or regenerate the spent fluids. Such a system can be straightforward in setup and can involve merely using a column-type setup wherein the spent fluids are passed from top to bottom wherein gravity permits the spent fluid to go through the cartridge or spent fluid can be passed through the cartridge under pressure which permits the spent fluids to be introduced in any direction.

Figure 13:
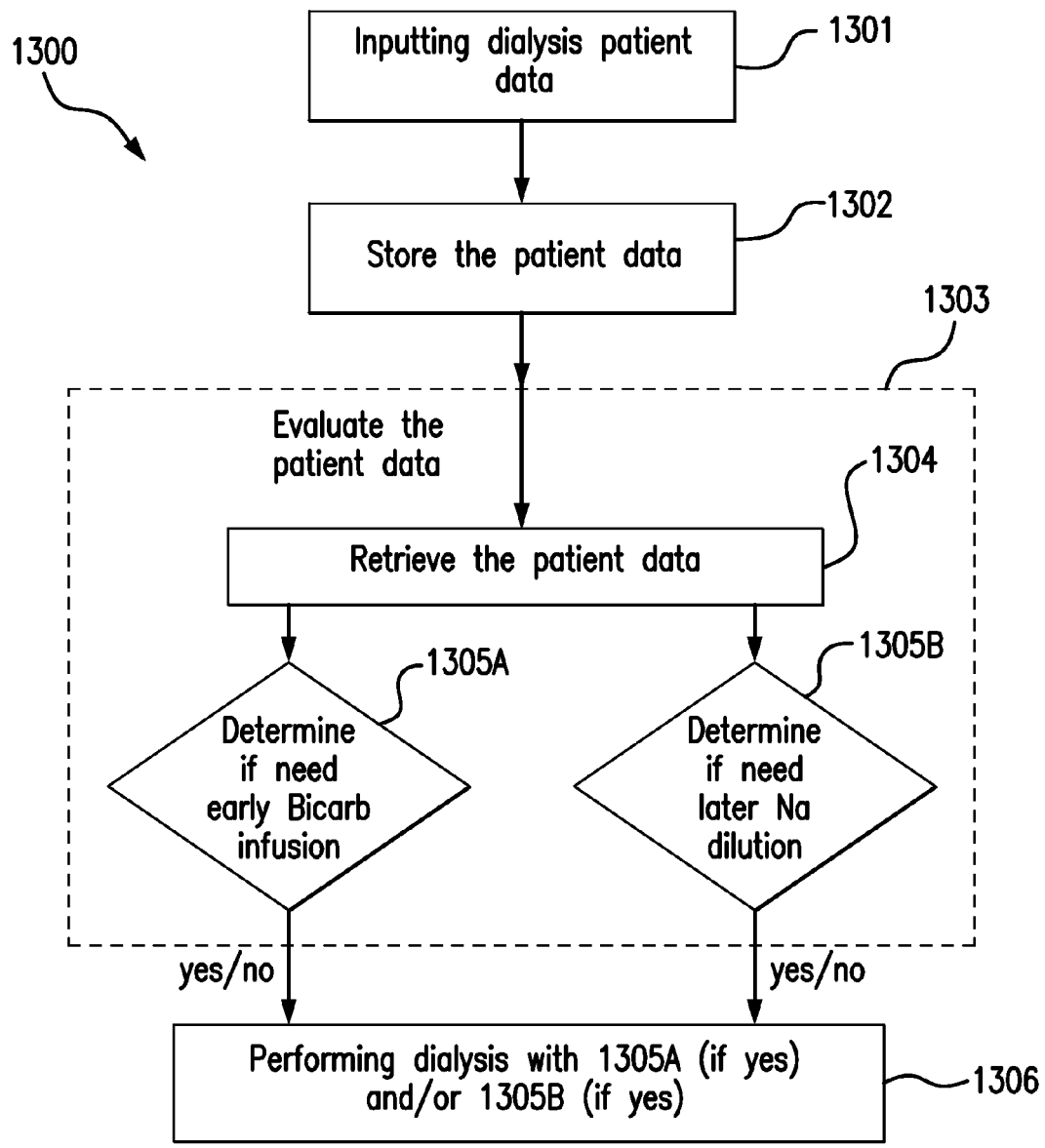
FIG. 13 shows a process flow diagram of a method for managing a pre-evaluation of patient for a dialysis treatment according to an example of the present application.

Referring to FIG. 13, a method for managing a pre-evaluation of patient for a dialysis treatment according to an example of the present invention is shown as process flow 1300, which includes steps 1301-1306. In step 1301, dialysis patient data is inputted into a central processing unit (CPU). The patient data can comprise, for example, urea donation data from dialysis treatment(s), body mass data, sodium serum data from dialysis treatment(s), and patient blood chemistry data, obtained from medical and/or dialysis treatment records of the patient. In step 1302, the patient data is stored in the CPU. In step 1303, a dialysis patient's data is evaluated prior to initiating a dialysis treatment session for the patient. The evaluation includes two substeps. In substep 1304, the patient data is retrieved from the CPU. In substeps 1305A and 1305B, it is determined if the patient needs bicarbonate addition in the initial dialysis 1) if the patient requires introduction of bicarbonate solution into regenerated dialysate during a first dialysis treatment time period to provide a treated regenerated dialysate that is circulated to the dialyzer and if so, further computing the introduction timing and rate needed thereof (substep 1305A), and 2) if the patient requires addition of sterile dilution water to the regenerated dialysate during a second dialysis treatment time period occurring after the first dialysis treatment time period to provide a diluted regenerated dialysate that is circulated to the dialyzer and if so, further computing the introduction timing and rate needed thereof (substep 1305B). In step 1306, dialysis is performed on the patient using any bicarbonate solution and/or sterile water introduction timing and rate computed in substeps 1305A and 1305B. The evaluating step can further comprise classifying patients into subgroups based on values computed in substeps 1305A and 1305B, wherein all patients assigned to a respective subgroup can receive the same predetermined bicarbonate solution and/or sterile water dilution treatment during a dialysis treatment session.

Figure 14:
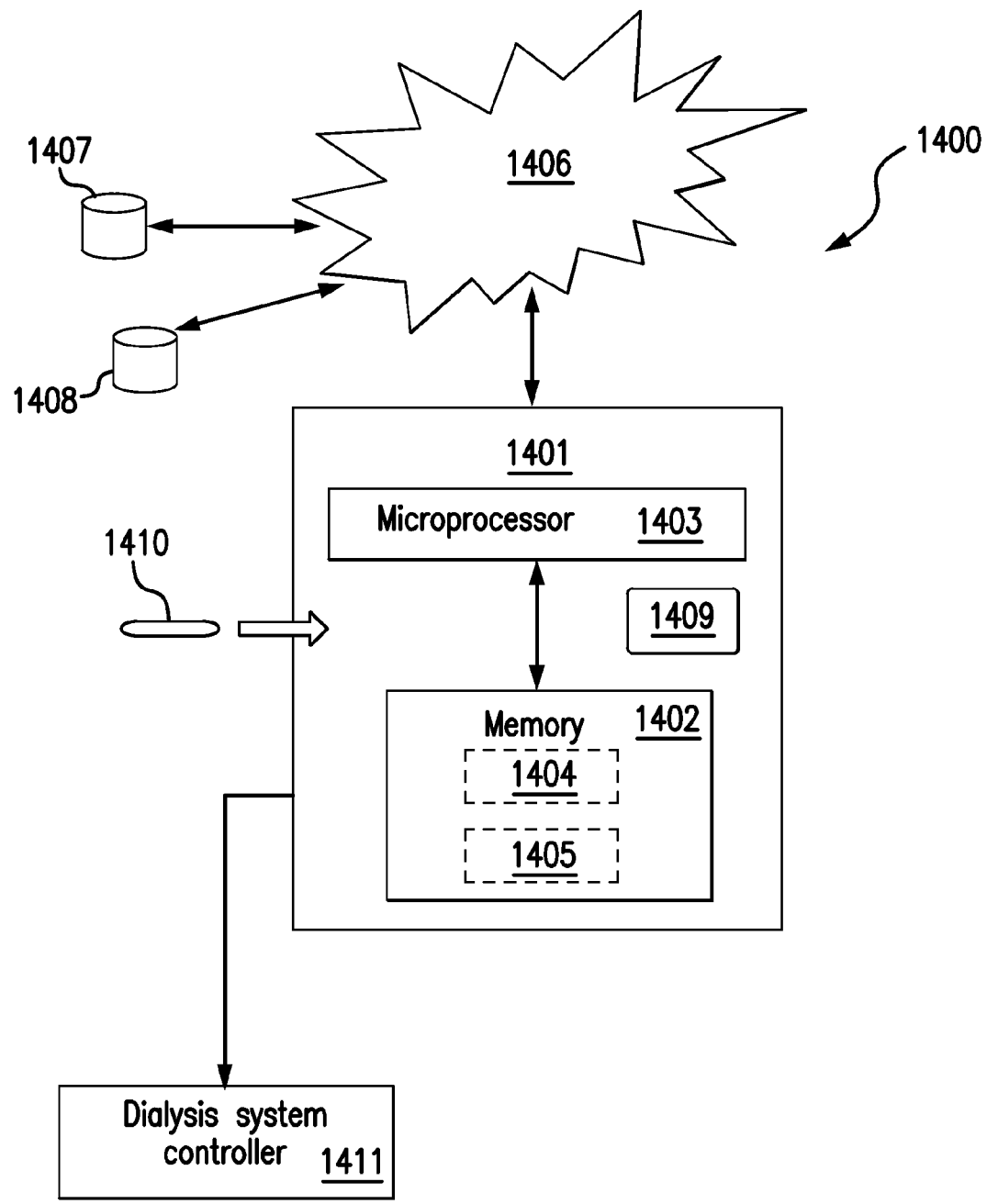
FIG. 14 shows a system for carrying out the method for managing the indicated pre-evaluation of patient for a dialysis treatment according to an example of the present application.

FIG. 14 shows a system for carrying out a method for pre-evaluating dialysis patients as part of treatments thereof. The system is indicated as the configuration 1400. A computer 1401 comprises at least one memory device 1402 and at least one (micro)processor 1403. The computer can be a laptop, desktop, handheld or server computing device. The computer can be equipped for hardwire and/or wireless communication of data, instructions, and other information. The at least one memory device 1402 is configured to have patient data 1404 inputted and stored therein. The patient data includes the above-indicated kinds. The at least one processor 1403 is operable for executing a computer program 1405 stored in the memory that is capable of performing computations based on retrieved patient data that is stored in the at least one memory device 1402. In order to acquire the patient data, the computer 1401 can communicate with a communications network 1406 which can be used to retrieve patient data from remote databases (1407, 1408, etc.) and/or transmit such information to external databases. The computer 1401 can communicate with remote databases using the communications network 1406 via hardwire (e.g., Ethernet, optical fiber, telephone, cable lines) and/or wirelessly (e.g., radio frequency, optically). The communications network 1406 can comprise the Internet (the world-wide network of computers generally accessible via an Internet Protocol (IP) address), intranet system (an internal network), and/or an extranet system (an Intranet that is partially accessible to authorised outsiders, e.g., the actual server (the computer that serves up the web pages) resides behind a firewall). One or more server computers can be included and used in the communications network. A cloud server may be used for data processing and/or execution of a program off-site. The patient data can be inputted directly to the memory 1402 of the computer 1401 via a graphical user interface using a keyboard 1409. The computer program(s) used for performing the computations of the pre-evaluation method of the present invention can be transferred into the computer 1401 using at least one non-transitory computer usable storage medium 1410 (e.g. a hard disk, a flash memory device, a compact disc, DVD, a magnetic tape/disk, or other media) or can be embodied by the computer. The computations performed by the computer using the computer program can determine 1) if the patient requires introduction of bicarbonate solution into regenerated dialysate during a first dialysis treatment time period to provide a treated regenerated dialysate that is circulated to the dialyzer and if so, further computing the introduction timing and rate needed thereof, and 2) if the patient requires addition of sterile water to the regenerated dialysate during a second dialysis treatment time period occurring after the first dialysis treatment time period to provide a diluted regenerated dialysate that is circulated to the dialyzer and if so, further computing the introduction timing and rate needed thereof. The computer 1401 is configured to communicate with a dialysis system controller 1411, such that signals or other instructions can be transmitted from the computer 1401 to the controller 1411 to manage the bicarbonate solution and/or sterile water dilution treatments if determined necessary by the indicated calculations and the regimens of such treatments (e.g., the timings, durations, dosages). The controller can be physical unit configured with hardware, firmware, software, and any combinations thereof. The controller 1411, or a separate controller(s), can be used to control other operations of the dialysis treatment. Those skilled in the art will appreciate that implementations of various techniques described herein may be practiced in a variety of computer system configurations, including hypertext transfer protocol (HTTP) servers, hand-held devices, multiprocessor systems, microprocessor-based or programmable consumer electronics, network PCs, mini-computers, mainframe computers, and the like.

The present invention will be further clarified by the following examples, which are intended to be only exemplary of the present invention. Unless indicated otherwise, all amounts, percentages, ratios and the like used herein are by weight.

The present invention includes the following aspects/embodiments/features in any order and/or in any combination:

1. A method of treating dialysate comprising:
    a) passing spent dialysate received from a dialyzer through a sorbent cartridge to produce regenerated dialysate that is discharged from the sorbent cartridge for circulation back to the dialyzer;
    b) introducing bicarbonate solution into the regenerated dialysate during a first dialysis treatment time period to provide a treated regenerated dialysate that is circulated to the dialyzer;
    c) adding sterile water to the regenerated dialysate during a second dialysis treatment time period occurring after the first dialysis treatment time period to provide a diluted regenerated dialysate that is circulated to the dialyzer.

2. The method of any preceding or following aspect/embodiment/feature, wherein the first dialysis treatment time period occurs within an initial 50% of total dialysis treatment time of a dialysis treatment session, and the second dialysis treatment time period occurs within a final 50% of the total dialysis treatment time of the same dialysis treatment session.

3. The method of any preceding or following aspect/embodiment/feature, wherein the introducing of the bicarbonate solution into the regenerated dialysate during the first dialysis treatment time period is at a rate to provide a treated regenerated dialysate with a bicarbonate concentration in a physiological range.

4. The method of any preceding or following aspect/embodiment/feature, wherein the introducing of the bicarbonate solution into the regenerated dialysate during the first dialysis treatment time period is at a rate to provide treated regenerated dialysate with a bicarbonate concentration in a range of 25-42 mEq/L, such as 33-38 mEq/L.

5. The method of any preceding or following aspect/embodiment/feature, wherein the first dialysis treatment time period is from 10% to 45% of total dialysis treatment time of a dialysis treatment session.

6. The method of any preceding or following aspect/embodiment/feature, wherein the dialysate passes through a fluid circuit comprising a first fluid circuit passageway extending between a spent dialysate outlet of the dialyzer to an inlet of the sorbent cartridge and a second fluid circuit passageway extending between an outlet of the sorbent cartridge to a regenerated dialysate inlet of the dialyzer, wherein, before starting a dialysis treatment session, (i) the fluid circuit is primed with precursor dialysate fluid containing from 0 to 0.1 wt % bicarbonate salt based on total weight of precursor dialysate fluid in the fluid circuit, and (ii) the sorbent cartridge contains from 0 to 1 wt % dry bicarbonate salt based on total weight of preloaded materials in the sorbent cartridge.

7. The method of any preceding or following aspect/embodiment/feature, wherein b) comprises metered pumping or orifice flow controller controlled feeding of concentrated bicarbonate solution or dry bicarbonate powder or bicarbonate powder from a source into a fluid circuit that is fluidly coupled thereto to infuse the concentrated sodium bicarbonate solution or bicarbonate powder or dry bicarbonate powder into the regenerated dialysate as the regenerated dialysate passes through the fluid circuit after being discharged from the sorbent cartridge and before introduction into the dialyzer.

8. The method of any preceding or following aspect/embodiment/feature, wherein the introducing of the sterile water to the regenerated dialysate during the second dialysis treatment time period is at a rate to provide a diluted regenerated dialysate with a sodium concentration in a physiological range.

9. The method of any preceding or following aspect/embodiment/feature, wherein the introducing of the sterile water to the regenerated dialysate during the second dialysis treatment time period is at a rate to provide a diluted regenerated dialysate with a sodium concentration in a range of 120-150 mEq/L, such as 139-144 mEq/L.

10. The method of any preceding or following aspect/embodiment/feature, wherein c) comprises delivering sterile water from a supply container through a tubing system into a fluid circuit through which the regenerated dialysate passes, wherein:

the supply container is arranged for gravitational flow of the sterile water into the tubing system, the tubing system comprises a first primary tube, an orifice flow controller, and a second primary tube, wherein i) the first primary tube fluidly connects the supply container and the orifice flow controller, wherein the first primary tube has a first inside diameter, ii) the second primary tube fluidly connecting the orifice flow controller and the fluid circuit, wherein the second primary tube has a second inside diameter, iii) the orifice flow controller defines an orifice having a reduced diameter relative to the first and second diameters, wherein flow of regenerated dialysate through the fluid circuit creating a fluid pressure differential via the orifice flow controller to induce flow of sterile water from the supply container through the tubing system into the fluid circuit.

11. The method of any preceding or following aspect/embodiment/feature, wherein the second dialysis treatment time period is from 10% to 45% of total dialysis treatment time of a dialysis treatment session.

12. The method of any preceding or following aspect/embodiment/feature, wherein no more than 2 liters of sterile water is introduced during the adding of the sterile water to the regenerated dialysate during the second dialysis treatment time period.

13. The method of any preceding or following aspect/embodiment/feature, wherein the sorbent cartridge comprises at least one activated carbon layer, at least one urease-containing layer, at least one zirconium phosphate-containing layer, and at least one zirconium oxide-containing layer.

14. The method of any preceding or following aspect/embodiment/feature, wherein the sorbent cartridge is free of a solid particulate bicarbonate layer.

15. The method of any preceding or following aspect/embodiment/feature, further comprising providing an expandable reservoir, first tubing, and second tubing, wherein the expandable reservoir comprising a reservoir inlet, a reservoir outlet, and a bottom portion defining progressively reducing cross-sectional area in a direction extending from the reservoir inlet towards the reservoir outlet, wherein fluid is held within the expandable reservoir in progressively smaller cross-sectional areas nearer to the reservoir outlet;

the second tubing configured to provide a fluid communication of regenerated dialysate discharged from the sorbent cartridge and any sterile water to the reservoir inlet; and the third tubing configured to provide a fluid communication of regenerated dialysate and any sterile water from the reservoir outlet to a dialysate inlet of the dialyzer.

16. A dialysis system for carrying out the method of any preceding or following aspect/embodiment/feature.

17. The present invention relates to a dialysis system comprising:

a dialyzer comprising a blood flow path, a dialysate flow path, a dialysate inlet for receiving fresh or regenerated dialysate into the dialyzer, and a dialysate outlet for discharging spent (used) dialysate from the dialyzer;

a sorbent cartridge configured for regenerating spent dialysate, the sorbent cartridge comprising a sorbent cartridge inlet and a sorbent cartridge outlet;

a fluid circuit comprising a first fluid passageway configured to provide fluid communication between the dialysate outlet of the dialyzer and the sorbent cartridge inlet, and a second fluid passageway configured to provide fluid communication between the sorbent cartridge outlet and the dialysate inlet of the dialyzer;

a source of bicarbonate solution which is fluidly coupled to the second fluid passageway;

a pump or orifice flow controller for delivery of the bicarbonate solution at a controlled rate from the source of bicarbonate solution into the second fluid passageway; and a supply of sterile water which is fluidly coupled to the second fluid passageway for introducing sterile water into the second fluid passageway from the supply container of sterile water.

18. The dialysis system of any preceding or following aspect/embodiment/feature, wherein the pump is present for delivery of the bicarbonate solution and is a programmable pump, such as a programmable syringe pump, and the supply of sterile water comprises a bag of sterile water that is hung at a raised position relative to the second fluid passageway for gravity feeding of the sterile water into the second fluid passageway.

19. The dialysis system of any preceding or following aspect/embodiment/feature, wherein the supply of sterile water comprises a container having a maximum volume of sterile water of about 2.0 liters or less.

20. The dialysis system of any preceding or following aspect/embodiment/feature, wherein the supply of sterile water comprises sterile water held in a container arranged for gravitational flow of the sterile water into the second fluid passageway, wherein the second fluid passageway comprises a tubing system, the tubing system comprises a first primary tube, an orifice flow controller, and a second primary tube, wherein i) the first primary tube fluidly connects the supply container and the orifice flow controller, wherein the first primary tube has a first inside diameter, ii) the second primary tube fluidly connecting the orifice flow controller and the fluid circuit, wherein the second primary tube has a second inside diameter, iii) the orifice flow controller defines an orifice having a reduced diameter relative to the first and second diameters, wherein flow of regenerated dialysate through the fluid circuit creating a fluid pressure differential relative to the supply of sterile water in the container to induce flow of sterile water from the supply of sterile water in the container through the tubing system into the fluid circuit at a controlled flow rate via the orifice flow controller.

21. The dialysis system of any preceding or following aspect/embodiment/feature, wherein the sorbent cartridge comprises at least one activated carbon layer, at least one urease-containing layer, at least one zirconium phosphate-containing layer, and at least one zirconium oxide-containing layer.

22. The dialysis system of any preceding or following aspect/embodiment/feature, wherein the sorbent cartridge is free of a solid particulate bicarbonate layer.

23. The dialysis system of any preceding or following aspect/embodiment/feature, further comprising an expandable reservoir, first tubing, and second tubing, wherein the expandable reservoir comprising a reservoir inlet, a reservoir outlet, and a bottom portion defining progressively reducing cross-sectional area in a direction extending from the reservoir inlet towards the reservoir outlet, wherein fluid is held within the expandable reservoir in progressively smaller cross-sectional areas nearer to the reservoir outlet;

the second tubing configured to provide a fluid communication of regenerated dialysate discharged from the sorbent cartridge and any sterile water to the reservoir inlet; and the third tubing configured to provide a fluid communication of regenerated dialysate and any sterile water from the reservoir outlet to the dialysate inlet of the dialyzer.

24. The dialysis system of any preceding or following aspect/embodiment/feature, wherein the source of bicarbonate solution and the supply of sterile water are controllable for dispensing or not.

25. The dialysis system of any preceding or following aspect/embodiment/feature, wherein the source of bicarbonate solution and the supply of sterile water are controllable for dispensing, and the source of bicarbonate solution and the supply of sterile water are controlled based on signals provided by a controller.

26. The dialysis system of any preceding or following aspect/embodiment/feature, wherein the controlling is based on if the patient needs one or other of the bicarbonate solution and the sterile water added to the dialysate.

27. The dialysis system of any preceding or following aspect/embodiment/feature, wherein the patient needing one or other of the bicarbonate solution and the sterile water added to the dialysate or not is based on pre-dialysis testing and/or prior patient history and/or using one or more pre-screening factors to determine expected needs of patient.

28. The present invention relates to a kit comprising:
  a first package, the first package containing
  a dialyzer comprising a blood flow path, a dialysate flow path, and a dialysate inlet and a dialysate outlet both in fluid communication with the dialysate flow path,
  a sorbent cartridge configured for regenerating used dialysate, the sorbent cartridge comprising a sorbent cartridge inlet and a sorbent cartridge outlet,
  a first tubing configured to provide a fluid communication between the dialysate outlet of the dialyzer and the sorbent cartridge inlet,
  an expandable reservoir comprising a reservoir inlet and a reservoir outlet,
  a second tubing configured to provide a fluid communication between the sorbent cartridge outlet and the reservoir inlet, and
  a third tubing configured to provide a fluid communication between the reservoir outlet and the dialysate inlet of the dialyzer;
  a second package, the second package containing
  a supply container containing from about 1.5 liters to about 2.0 liters of sterile water, first primary tube, an orifice flow controller, and a second primary tube, wherein the first primary tube is configured to fluidly connect the sterile water supply container and the orifice flow controller, and the second primary tube is configured to connect the venture constrictor with the second tubing;
  a third package, the third package containing
  a supply container comprising a container containing pumpable concentrated bicarbonate solution or a container containing dry bicarbonate powder wherein the container has a water inlet which allows entry of purified water and an outlet from which concentrated bicarbonate solution exits, and first bicarbonate carrying tubing for delivery of the concentrated bicarbonate solution to a pump or orifical flow controller and/or second bicarbonate carrying tubing for delivery of the concentrated bicarbonate solution from the pump or orifice flow controller to the third tubing, and optionally an orifice flow controller.

29. The present invention relates to a method for pre-evaluating dialysis patients as part of treatments thereof, comprising:
  a) inputting dialysis patient data into a central processing unit (CPU), wherein the patient data comprises urea donation data during dialysis treatment(s), body mass data, sodium serum data during dialysis treatment(s), and patient blood chemistry data, obtained from medical and/or dialysis treatment records of the patient;
  b) storing the patient data in the CPU;
  c) evaluating a dialysis patient prior to initiating a dialysis treatment session for the patient, comprising
    i) retrieving the patient data from the CPU,
    ii) determining 1) if the patient requires introduction of bicarbonate solution into regenerated dialysate during a first dialysis treatment time period to provide a treated regenerated dialysate that is circulated to the dialyzer and if so, further computing the introduction timing and rate needed thereof, and 2) if the patient requires addition of sterile water to the regenerated dialysate during a second dialysis treatment time period occurring after the first dialysis treatment time period to provide a diluted regenerated dialysate that is circulated to the dialyzer and if so, further computing the introduction timing and rate needed thereof; and
  d) performing dialysis on the patient using any bicarbonate solution and/or sterile water introduction timing and rate computed in step c).

30. The method of any preceding or following aspect/embodiment/feature, wherein the evaluating further comprising classifying patients into subgroups based on values computed in step c)ii), wherein all patients assigned to a respective subgroup receive the same predetermined bicarbonate solution and/or sterile water dilution treatment during a dialysis treatment session.

31. The present invention relates to a system for pre-evaluating dialysis patients as part of treatments thereof, comprising:
  a computer comprising at least one memory device and at least one processor, wherein
  the at least one memory device configured to have patient data inputted and stored therein, wherein the patient data comprising urea donation data from dialysis treatment(s), body mass data, sodium serum data from dialysis treatment(s), patient blood chemistry data, obtained from medical and/or dialysis treatment records of the patient;
  the at least one processor operable for executing a computer program capable of performing computations based on retrieved patient data from the at least one memory device, wherein the computations determining 1) if the patient requires introduction of bicarbonate solution into regenerated dialysate during a first dialysis treatment time period to provide a treated regenerated dialysate that is circulated to the dialyzer and if so, further computing the introduction timing and rate needed thereof, and 2) if the patient requires addition of sterile dilution water to the regenerated dialysate during a second dialysis treatment time period occurring after the first dialysis treatment time period to provide a diluted regenerated dialysate that is circulated to the dialyzer and if so, further computing the introduction timing and rate needed thereof.

32. The present invention relates to a non-transitory computer readable medium with a computer program product embodied thereon, wherein when the computer program product is performed on a processor in a computerized device provides a method for performing computations of one or more or all of the indicated steps of the method of any preceding or following aspect/embodiment/feature.

The present invention can include any combination of these various features or embodiments above and/or below as set forth in sentences and/or paragraphs. Any combination of disclosed features herein is considered part of the present invention and no limitation is intended with respect to combinable features.

The entire contents of all references cited in this disclosure are incorporated herein in their entireties, by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A dialysis system comprising:
   a dialyzer comprising a blood flow path, a dialysate flow path, a dialysate inlet for receiving fresh or regenerated dialysate into the dialyzer, and a dialysate outlet for discharging spent (used) dialysate from the dialyzer;
   a sorbent cartridge configured for regenerating spent dialysate, the sorbent cartridge comprising a sorbent cartridge inlet and a sorbent cartridge outlet;
   a fluid circuit comprising a first fluid passageway configured to provide fluid communication between the dialysate outlet of the dialyzer and the sorbent cartridge inlet, and a second fluid passageway configured to provide fluid communication between the sorbent cartridge outlet and the dialysate inlet of the dialyzer;
   a source of bicarbonate solution which is fluidly coupled to the second fluid passageway;
   a pump or orifice flow controller for delivery of the bicarbonate solution at a controlled rate from the source of bicarbonate solution into the second fluid passageway wherein said orifice flow controller having a body that defines an orifice or flow passageway through which fluid flows from tubing fluidly coupled at an inlet of the orifice flow controller to tubing fluidly coupled at the outlet of the orifice flow controller; and
   a supply of sterile water which is fluidly coupled to the second fluid passageway for introducing sterile water into the second fluid passageway from the supply container of sterile water wherein the pump or orifice flow controller is controlled by an electronic controller, which is configured to introduce the bicarbonate into the regenerated dialysate during a first dialysis treatment time period to provide a treated regenerated dialysate that is circulated to the dialyzer; and said supply of sterile water is controlled by the same or different electronic controller, such that the sterile water is added to the regenerated dialysate during a second dialysis treatment time period occurring after the first dialysis treatment time period to provide a diluted regenerated dialysate that is circulated to the dialyzer and wherein the first dialysis treatment time period occurs within an initial 50% of total dialysis treatment time of a dialysis treatment session, and the second dialysis treatment time period occurs within a final 50% of the total dialysis treatment time of the same dialysis treatment session.

2. The dialysis system of claim 1, wherein the pump is present for delivery of the bicarbonate solution and is a programmable pump, and the supply of sterile water comprises a bag of sterile water that is hung at a raised position relative to the second fluid passageway for gravity feeding of the sterile water into the second fluid passageway.

3. The dialysis system of claim 1, wherein the supply of sterile water comprises a container having a maximum volume of sterile water of about 2.0 liters or less.

4. The dialysis system of claim 1, wherein the supply of sterile water comprises sterile water held in a container for flow of the sterile water into the second fluid passageway, wherein the second fluid passageway comprises a tubing system,
   the tubing system comprises a first primary tube, an orifice flow controller, and a second primary tube, wherein i) the first primary tube fluidly connects the supply container and the orifice flow controller, wherein the first primary tube has a first inside diameter, ii) the second primary tube fluidly connecting the orifice flow controller and the fluid circuit, wherein the second primary tube has a second inside diameter, iii) the orifice flow controller defines an orifice having a reduced diameter relative to the first and second diameters, wherein flow of regenerated dialysate through the fluid circuit creating a fluid pressure differential relative to the supply of sterile water in the container to induce flow of sterile water from the supply of sterile water in the container through the tubing system into the fluid circuit at a controlled flow rate via the orifice flow controller.

5. The dialysis system of claim 1, wherein the sorbent cartridge comprises at least one activated carbon layer, at least one urease-containing layer, at least one zirconium phosphate-containing layer, and at least one zirconium oxide-containing layer.

6. The dialysis system of claim 5, wherein the sorbent cartridge is free of a solid particulate bicarbonate layer.

7. The dialysis system of claim 1, further comprising an expandable reservoir, first tubing, and second tubing, wherein
   the expandable reservoir comprising a flexible bag having a reservoir inlet, a reservoir outlet, and a bottom portion defining progressively reducing cross-sectional area in a direction extending from the reservoir inlet towards the reservoir outlet, wherein fluid is held within the expandable reservoir in progressively smaller cross-sectional areas nearer to the reservoir outlet;

the second tubing configured to provide a fluid communication of regenerated dialysate discharged from the sorbent cartridge and any sterile water to the reservoir inlet; and a third tubing configured to provide a fluid communication of regenerated dialysate and any sterile water from the reservoir outlet to the dialysate inlet of the dialyzer.

8. The dialysis system of claim 1, wherein the source of bicarbonate solution and the supply of sterile water are controllable for dispensing or not dispensing.

9. The dialysis system of claim 8, wherein the source of bicarbonate solution and the supply of sterile water are controllable for dispensing, and the source of bicarbonate solution and the supply of sterile water are controlled based on signals provided by a controller.

10. The dialysis system of claim 9, wherein the controlling is based on if the patient needs one or other of the bicarbonate solution and the sterile water added to the dialysate.

11. The dialysis system of claim 10, wherein the patient needing one or other of the bicarbonate solution and the sterile water added to the dialysate or not is based on pre-dialysis testing and/or prior patient history and/or using one or more pre-screening factors to determine expected needs of patient.

* * * * *